United States Patent [19]

Giordano et al.

[11] Patent Number: 4,697,036
[45] Date of Patent: Sep. 29, 1987

[54] PROCESS FOR THE PREPARATION OF OPTICALLY ACTIVE ALPHA-ARYLALKANOIC ACIDS AND NOVEL INTERMEDIATES THEREOF

[75] Inventors: Claudio Giordano, Vicenza; Graziano Castaldi, Briona; Fulvio Uggeri, Codogno; Silvia Cavicchioli, Costermano, all of Italy

[73] Assignee: Zambon S.P.A., Vincenza, Italy

[21] Appl. No.: 720,380

[22] Filed: Apr. 5, 1985

[30] Foreign Application Priority Data

Apr. 6, 1984 [IT] Italy .................................. 7204 A/84
Aug. 6, 1984 [IT] Italy .................................. 7206 A/84
Aug. 6, 1984 [IT] Italy .................................. 7207 A/84

[51] Int. Cl.$^4$ ............................................. C07C 51/16
[52] U.S. Cl. ..................................... 562/418; 549/60;
549/450; 548/517; 548/523; 546/207; 546/208;
544/374; 544/372; 544/148; 544/141; 560/55;
560/81
[58] Field of Search ................... 560/55, 81; 549/450,
549/60; 548/517, 523; 546/207, 208; 544/374,
372, 148, 141; 562/418, 419, 407

[56] References Cited

U.S. PATENT DOCUMENTS 2,249,519  7/1941  Dickey et al. ...................... 549/450
3,215,728  11/1965 Meier et al. ........................ 560/81
3,763,229  10/1973 Noguchi et al. .................... 560/81
4,107,439  8/1978  Walker et al. ....................... 560/55

FOREIGN PATENT DOCUMENTS 0034781  9/1981  European Pat. Off. ............. 549/455
158913  10/1985 European Pat. Off. ............. 549/450
46-40614 12/1971 Japan ................................... 560/81

Primary Examiner—Nicky Chan
Attorney, Agent, or Firm—Cushman, Darby & Cushman

[57] ABSTRACT

A new enantioselective process is described for preparing optically active alpha-arylalkanoic acids by:
(a) halogenation on the aliphatic carbon atom alpha to the ketal group, of ketals of formula

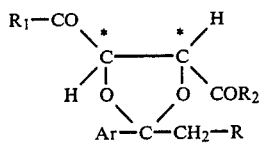

in which
Ar represents an aryl, optionally substituted;
R represents a $C_1$-$C_4$ alkyl;
$R_1$ and $R_2$, represents a hydroxy, a $O^- M^+$, $OR_3$ or $NR_4R_5$ group; the carbon atoms indicated by an asterisk both simultaneously are in (R) or (S) configuration.

This reaction is diastereoselective, so that a misture of alpha-haloketals is obtained in which one of the two epimers prevails, and generally strongly prevails, over the other.
(b) rearrangement of the haloketals of formula

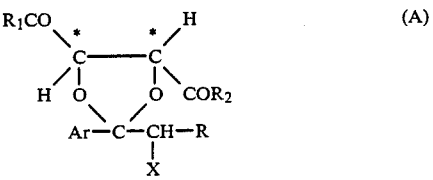

(A)

in which X is Cl, Br or I to alpha-arylalkanoic acids in a single stage or in two successive stages, by way of esters of formula

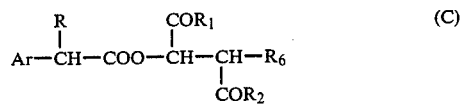

(C)

The compounds (A) and (C) are all new compounds.

The rearrangement step (b) may be performed under new, inventive conditions.

The esters of formula (C) have pharmacological activity analogous to that of the corresponding alpha-arylalkanoic acids.

8 Claims, No Drawings

PROCESS FOR THE PREPARATION OF OPTICALLY ACTIVE ALPHA-ARYLALKANOIC ACIDS AND NOVEL INTERMEDIATES THEREOF

The present invention relates to a process for preparing optically active alpha-arylalkanoic acids and the novel intermediates thereof. In particular, the present invention concerns an overall enantioselective process for the preparation of optically active alpha-arylalkanoic acids comprising two main steps: a stereoselective halogenation of novel chiral (optically active) ketals and a stereoselective rearrangement of the thus obtained products.

The alpha-arylalkanoic acids constitute a very large class of compounds, of which many have assumed considerable commercial importance in relatively recent years as anti-inflammatory and analgesic drugs.

These include 2-(4-isobutylphenyl)-propionic acid known as Ibuprofen, 2-(3-phenoxyphenyl)-propionic acid known as Fenoprofen, 2-(2-fluoro-4-diphenyl)-propionic acid known as Flurbiprofen, 2-[4-(2-thienylcarbonyl)-phenyl]-propionic acid known as Suprofen, 2-(6-methoxy-2-naphthyl)-propionic acid, of which the (S) isomer is known as Naproxen, and others.

Another group of alpha-arylalkanoic acids are well known as intermediates in the preparation of pyrethroid insecticides. These include 2-(4-chlorophenyl)-3-methyl-butyric acid and 2-(4-difluoromethoxyphenyl)-3-methyl-butyric acid.

A number of the alpha-arylalkanoic acids exist as a mixture of optically active isomers.

Very often, a decidedly higher biological activity is associated with one enantiomer which thus is much more important than the other from an industrial viewpoint.

A particularly important example is 2-(6-methoxy-2-naphthyl)-propionic acid, of which the (S) isomer (Naproxen) possesses pharmacological properties which are decidedly better than those of the (R) isomer and of the raceme mixture, so that in practice it is only the (S) isomer which is used as pharmaceutical drug.

Of the many methods for synthesising alpha-arylalkanoic acids which have recently appeared in the literature, the most interesting are those which use rearrangement of aryl-alkyl-ketals which are functionalised on the alkyl position alpha to the ketal. These include the methods described in European patent applications 34871 (Blaschim), 35305 (Blaschim), 48136 (Sagami), 64394 (Syntex), 89711 (Blaschim), and 101124 (Zambon), and in Italian patent applications 21841 A/82 (Blaschim and CNR), 22760 A/82 (Zambon) and 19438 A/84 (Zambon), and in the publication J. Chem. Soc., Perkin I, 11, 2575 (1982). All these processes lead to racemic mixtures of the two optical isomers.

Optically active alpha-arylalkanoic acids can be prepared by separating the enantiomer from the racemic mixture obtained by using the aforesaid procedures (for example by using optically active bases), or by applying some of said rearrangements to optically active ketals, which have been previously prepared and isolated, as described for example in European patent applications 67698 (Sagami) and 81993 (Syntex).

However, the preparation of optically active ketals as described in these European patent applications appears rather laborious and costly, and also involves the preparations of intermediates by sophisticated methods with low yields, and are not suitable for industrial preparation.

The resolution of alpha-arylalkanoic acids from the racemic mixture in a conventional way, that is by using optically active bases has the drawbacks common to all these processes: material costs, manufacturing labor and equipment for the recovery and racemization of the undesired optical isomer.

Therefore, it is important to have a stereoselective process for producing the desired isomer directly. Such a process obviates the necessity of subsequently resolving the d- and l-isomers using optically active bases, such as cinchonidine, brucine, alpha-phenylethylamine, N-methyl-glucamine and the like.

The elimination of resolution steps results in a substantial saving, both in material cost and manufacturing labor and equipment. The savings can be particularly significant with regard to compounds which are approved for pharmaceutical use as a substantially pure, optically active isomer, such as S(+)2-(6-methoxy-2-naphtyl)-propionic acid (Naproxen) or a precursor thereof which may be easily converted to this acid.

For the sake of clarity we will state hereinafter the meaning of some terms used in the following specification:

"Chiral" refers to a chemical structure having at least an asymmetry center. The configuration of an asymmetric carbon atom is classified as "R" or "S" according to the Cahn-Ingold-Prelog method.

"Enantiomer" or "enantiomorph" refers to a molecule which is nonsuperimposable on its respective mirror image. A necessary and sufficient condition for a molecule to show optical activity (i.e. to be an enantiomer) is that such a molecule not be superimposable with its mirror image. This phenomenum usually occurs in organic chemistry when a carbon atom is attached to four different atoms or chemical groups. "Enantiomer" and "optical isomer" are often used interchangeably in this context.

"Enantiomeric excess" or "e.e." refers to a definition; i.e. the percentage of the predominant enantiomer minus that of the other. Thus, a mixture of 95% (+) isomer and 5% (−) isomer would have a 90% e.e.

"Optical yield" or "optical purity" may be defined as enantiomeric excess. However, strictly speaking, it refers to the measured rotation shown by the mixture which may or may not reflect the true proportions of the enantiomers. In this application the two terms are used interchangeably.

"Optically active" refers to a system or compound which rotates the plane of polarized light.

"Epimers" are two diastereoisomers which have a different configuration at only one chiral center.

"Diastereoisomers" are stereoisomers that are not mirror images of each other: they have the same configuration at at least one asymmetric center and, at the same time, different configuration at at least one asymmetric center.

"Diastereotopic" refers to the case in which two atoms or groups in a molecule e.g. $CX_2WY$ are in such a position that replacing each of them by a group Z leads to diastereoisomers.

"Stereoselective synthesis" refers to any reaction in which one among a number of stereoisomers is formed exclusively or predominantly.

"Enantioselective synthesis" refers to any reaction in which one of two enantiomers is formed exclusively or predominantly.

"Racemization" refers to the conversion of the molecules on one enantiomer into a racemic mixture of both.

We have now prepared and are an object of the present invention, new ketals of alkyl-aryl-ketones of formula:

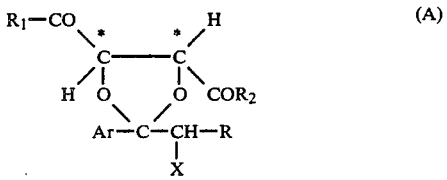

in which:

Ar represents aryl, optionally substituted;

R represents linear or branched $C_1$-$C_4$ alkyl; $R_1$ and $R_2$, which can be equal to or different from each other, represent a hydroxy, a $O^-M^+$, $OR_3$ or $NR_4R_5$ group where $R_3$ is $C_1$-$C_{24}$ alkyl, $C_3$-$C_6$ cycloalkyl, phenyl or benzyl; M is the cation of an alkaline metal; $R_4$ and $R_5$, which can be equal to or different from each other, represent a hydrogen atom, a $C_1$-$C_4$ alkyl, a $C_5$-$C_6$ cycloalkyl, or a —$(CH_2)_n$—$CH_2OH$ group where n is 1, 2 or 3 or $R_4$ and $R_5$ taken together constitute a —$(CH_2)_m$— group where m is 4 or 5 or a —$CH_2$—$CH_2$—$R_7$—$CH_2$—$CH_2$— group where $R_7$ is an oxygen atom, a NH group or a $C_1$-$C_4$ N-alkyl group; X represents a hydrogen, chlorine, bromine or iodine atom. The carbon atoms indicated by an asterisk are both contemporaneously in (R) or (S) configuration. Thus the ketals of formula A are optically active.

The ketals of formula (A) have shown quite unexpected properties which allow the realization of the new process according to the present invention.

In fact, we have found that when ketals of formula A, in which X is hydrogen, are reached with achiral halogenating reagents, a chemoselective halogenation occurs in high yield on the diastereotopic carbon atom in the alpha position with respect to the ketal group and in the thus obtained alpha halogen ketals (formula A, X=Cl, Br, I) only one of the epimers is formed or strongly prevails over the other. It is worth noting that the absolute configuration (R,R or S,S) of the chiral centers already present on the starting ketals A (Z=H) is untouched. As far as we know, a stereoselective halogenation in the alpha position of a ketal has never been previously described.

Moreover, we have found that the ketals of formula A in which X=Cl, Br, I provide in high yields alpha-arylalkanoic acids in which the enantiomeric ratio reflects the epimeric ratio of the starting ketals or, depending on the rearrangement conditions, the acid enantiomeric ratio is higher than the epimeric ratio of the starting ketals.

To our knowledge, it is the first time that a rearrangement of ketals is described which gives rise to chemically pure alpha-arylalkanoic acids having an enantiomeric excess higher than the epimeric excess of the starting ketals.

Thus a further object of the present invention is an enantioselective process for the preparation of alpha-aryl-alkanoic acids by diastereoselective halogenation, in the alpha position to the ketal group, of otically active ketals of formula (A) wherein X=H and the enantioselective rearrangement of the obtained halo-ketals into the corresponding alpha-arylalkanoic acids.

An enantioselective process for preparing optically active alpha-arylalkanoic acids is completely new.

The arylalkanoic acids prepared according to the present invention fall within the formula

in which R is a $C_1$-$C_4$ alkyl; Ar is as heretofore defined and preferably a monocyclic, polycyclic, or orthocondensed polycyclic aromatic or heteroaromatic group having up to 12 carbon atoms in the aromatic system such as phenyl, diphenyl, naphthyl, thienyl, or pyrrolyl. The possible substituents of these aromatic groups comprise one or more halogen atoms, $C_1$-$C_4$ alkyls, $C_3$-$C_5$ cycloalkyls, benzyl, hydroxy, $C_1$-$C_4$ alkoxy, $C_1$-$C_4$ alkylthio, $C_1$-$C_4$ haloalkyl, $C_1$-$C_4$ haloalkoxy, phenoxy, thienylcarbonyl and benzoyl.

Specific examples of such substituted aryls are 4-isobutyl-phenyl, 3-phenoxy-phenyl, 2-fluoro-4-diphenyl, 4'-fluoro-4-diphenyl, 4-(2-thienylcarbonyl)-phenyl, 6-methoxy-2-naphthyl, 5-chloro-6-methoxy-2-naphthyl and 5-bromo-6-methoxy-2-naphthyl, 4-chloropehnyl, 4-difluoromethoxy-phenyl, 6-hydroxy-2-naphthyl, and 5-bromo-6-hydroxy-2-naphthyl.

The ketals of formula (A) which constitute the starting compounds for the new process according to the present invention are prepared by ketalization of a ketone of formula

(in which Ar and R have the aforesaid meanings) by means of L(+)-tartaric acid (2R, 3R-dihydroxybutanedioic acid) or D(—)-tartaric acid (2S, 3S-dihydroxybutanedioic acid) or derivatives thereof.

The ketones of formula II are products which are known or are easily prepared by known methods, for example by Friedel-Crafts acylation. The ketalization reaction is carried out according to conventional methods, for example in the presence of an acid catalyst and an orthoester. Alternatively, the water formed during the reaction can be removed by azeotropic distillation, for example with benzene, toluene, xylene, heptane or other suitable solvents. The absolute configuration and the optical purity of the ketals of formula A in which X is hydrogen are the same as those of the starting diol (tartaric acid or derivative thereof). Thus, starting from L(+)-tartaric acid, the obtained ketal of formula A has both the carbon atoms marked by an asterisk in formula A hereabove in the R configuration.

This reaction is particularly suitable for preparing compounds of formula (A) in which $R_1$ and $R_2$ represent a $OR_3$ group, by reacting the ketones of formula (II) with a tartaric acid ester. The ketals of formula (A) in which $R_1$ and $R_2$ are other than $OR_3$ are preferably prepared starting from these latter compounds by suitable transformation of the $OR_3$ group.

For example, starting from esters of formula (A) in which $R_1$ and $R_2$ are $OR_3$ groups, the corresponding mono-salts (for example $R_1$=$O^+M^+$ and $R_2$=$OR_3$) can be prepared by partial saponification with one equivalent of a base (for example alkaline hydroxide), and from these the corresponding mono-acids (for example $R_1=OH$, $R_2=OR_3$) can be prepared by acidification.

Hydrolysis of the esters with two equivalents of an alkaline base leads to the formation of the corresponding salts ($R_1=R_2=O^-M^+$) which by acidification produce the free dicarboxylic acids ($R_1=R_2=OH$) which are the starting compounds for preparing different derivatives such as other mono or di-esters ($R_1$ and/or $R_2=OR_3$) or mono or di-amides ($R_1$ and/or $R_2=NR_4R_5$).

The amides can also be obtained directly from the esters of formula (A) by treatment with a suitable amine of formula $R_4R_5$-N-H. As stated heretofore, the compounds (A) wherein X=H are useful as the starting compounds for preparing the compounds of formula (A) in which X represents a chlorine, bromine or iodine atom.

The compounds of formula (A) are halogenated by known halogenating agents for example bromine, quaternary ammonium perhalides, sulphuryl chloride, cupric chloride or bromide, N-bromo or N-chlorosuccinimide, N-chloro-phthalimide, pyridine or pyrrolidone perbromide or pyridine perchloride or the analogous iodides, hexachloro-2,4-cyclohexadienone, iodine and iodide chloride, or analogous systems.

We have found that the halogenation of ketals having the carbon atoms marked by an asterisk in formula A hereabove both in configuration R, that is ketals prepared from L(+)-tartaric acid or a derivative thereof (i.e. the naturally occurring tartaric acid), give rise to the formation of a mixture of epimeric alpha-halo ketals in which the epimer in which the carbon atom bonded to the halogen is in the S configuration, strongly prevails. Since the configuration of the carbon atoms marked by an asterisk in formula A hereabove remains unchanged, the major epimer of the alpha haloketals derived from the naturally occurring tartaric acid or a derivative thereof, will be hereinafter referred to as RRS epimer and the minor one as RRR epimer.

We have also found that starting from ketals derived from D(−)-tartaric acid, the major epimer has the carbon atom bonded to the halogen atom in the R configuration.

From the above findings it clearly results that the described halogenation reaction is a new stereoselective reaction.

The ratio between the epimers RRS/RRR is generally higher than 75:25 and in most of the cases is higher than 94:6. Depending on the substrate and the reaction conditions it is also possible to obtain the RRS epimer as the only chemically pure alpha-halogen-ketal, the other epimer RRR present, if any, in an amount lower than 1%.

Generally, the yields in alpha-halogen ketals are higher than 90%.

The stereoselectivity of the halogenation reaction is only slightly affected by the polarity of the solvent. A number of solvents such as carbon tetrachloride, 1,2-dichloroethane, chlorobenzene, benzene, toluene, acetonitrile, cyclohexane, ethylacetate, carbon disulphide, acetic acid and so on, may be used. Best results are obtained by using solvents of low polarity. The reaction may be carried out at room temperature with satisfactory results. The stereoselectively of the halogenation reaction increases by lowering the reaction temperature. The reaction still occurs up to −70° C.

Preferably, traces of a mineral acid are required to start-up the halogenation reaction which is usually terminated in a few minutes. As far as yields and stereoselectivity are concerned, the preferred halogenation reaction is the bromination. Said reaction is preferably carried out with bromine as the halogenating agent, at a temperature between −40° and +20° C. in solvents such as carbon tetrachloride, methylene chloride, 1,2-dichloro-ethane and carbon disulphide.

The peculiar characteristics of the ketals of formula A and in particular the shown high stereoselectivity in the halogenation reaction, were completely unpredictable on the base of the present knowledge of stereocontrolled reactions.

Independently from the aforesaid, the fact that the ketals of formula (A) where X=halogen exist in the form of diastereoisomers easily separable by known methods, for example by fractional crystallization, is also important.

If required, it is therefore possible to separate the desired isomer of the ketal of formula (A) and subject this to rearrangement to obtain the alpha-arylalkanoic acid in the substantially pure optically active form.

It is also important to note that tartaric acids and esters, in particular L(+)-tartaric acid and the relative methyl and ethyl esters, have a commercial cost which is competitive with that of the glycols described as ketalizing agents in the processes of the known art, and the preparation of the tartaric acid derivatives (ester, amides, salts) certainly does not constitute a costly process.

The possibility of having groups of different nature in the ketals of formula A, with reference to the substituents $R_1$ and $R_2$, enables to vary the hydrophilic and lipophilic properties of said ketals within wide limits, from compounds containing polar grups (alkaline salts, amides) to lipophilic compounds (esters of long-chain alcohols).

This wide possibility of choice allows to select the ketal of formula A most suitable for the experimental conditions (solvents, temperature, catalysts) used in the various processes for the preparation of alpha-arylalkanoic acids or their derivatives by rearrangement.

As far as the rearrangement of the ketals of formula A (in which X=Cl, Br, I) is concerned, we have found that the ketals having the configuration RRS (wherein S is the configuration of the carbon atom bonded to the halogen atom) provide the S-enantiomer of the corresponding alpha-arylalkanoic acid.

This is particularly important because (a) the S-enantiomer of alpha-arylalkanoic acid is generally the biologically more active isomer and the alpha-arylalkanoic acids present on the market in optically active form are all of S-configuration and because (b) the ketals of formula A having configuration RRS are selectively obtained by halogenation of the ketals of formula A, X=H in turn easily prepared from the appropriate ketone and the naturally occurring L(+)-tartaric acid (or a derivative thereof) which is a really unexpensive material.

In order to conveniently transform the optically active ketals of formula A (X=Cl, Br, I) it is necessary to use a rearrangement method which provides optically active alpha-arylalkanoic acids having an enantiomeric ratio very close to that of the epimers in the starting ketals. This implies that the reaction has to be stereospecific and that the reaction conditions are such that no racemization occurs in the final products. We have found that the known methods provide alpha arylalkanoic acids having enantiomeric ratio equal to or lower than the epimeric ratio of the starting ketals. We have also found, and this is a further object of the present invention, a new enantioselective rearrangement method which overcomes the above limits.

Such a process is herewith defined as enantioselective in so far as the enantiomeric composition (ratio between enantiomers S and R) of the alpha-arylalkanoic acids thus obtained, differs from the epimeric composition of the starting ketals of formula A and more precisely and quite surprisingly corresponds to an increase in the optical purity of the alpha-arylalkanoic acid with respect to the epimeric composition of the starting ketals.

Thanks to this new, surprising rearrangement process, starting from e.g. a mixture of epimeric ketals of formula A (in which X=Cl, Br, I) sufficiently enriched in the RRS epimer, it is possible to obtain in an optically pure form the S-enantiomer of the corresponding alpha-arylalkanoic acid.

It is worth noting that the yield of the new rearrangement process is as high as 80-90%.

The enantioselective process object of the present invention essentially consists in rearranging a ketal of formula A in which X is a chlorine, bromine or iodine atom, in aqueous medium at an acid pH, at a temperature comprised between room temperature and 100° C. The above mentioned rearrangement conditions are particularly unexpected and surprising in that it is well known that the treatment of a ketal with water under acidic conditions is a general method to convert ketals into the corresponding ketones and the alcohol or diol. Accordingly, the previously known alpha-haloalkylaryl ketals, under the above reaction conditions, undergo a fast hydrolysis providing the corresponding alpha haloalkyl-arylketone and alcohol or diol.

On the contrary, the ketals of formula A object of the present invention, when treated in aqueous acid medium, provide in high yield the corresponding alpha-arylakanoic acids, ketones being present, if any, in negligeable amounts.

The rearrangement process object of the invention is preferably carried out by using ketals of formula A (in which X=Cl, Br, I) soluble or at least partially soluble in water under the reaction conditions, i.e. the ketals of formula A in which $R^1$ and/or $R^2$ are hydrophilic groups.

The rearrangement is preferably carried out by heating the ketal of formula A in water at a pH comprised between 3.5 and 6.5. The desired pH values may be maintained by adding a suitable amount of a buffer.

The reaction duration depends mainly on the nature of the ketal of formula A, and on the reaction temperature. Generally, a high conversion degree is reached after some hours.

Usually, the alpha-arylalkanoic acids are scarcely soluble in water, therefore at the end of the reaction the optically active alpha-arylalkanoic acid may be isolated by simple filtration. A pharmaceutical product as pure as required by U.S. Pharmacopeia is obtained by simple acid-base treatment of the product isolated by filtration. As far as we know, this is the first time that a rearrangement of halogenketals for the preparation of alpha-arylalkanoic acids is carried out in water as the only reaction solvent. The main advantages of the present rearrangement process from an industrial point of view, may be summarized as follows: (a) the process is enantioselective and provides alpha-arylalkanoic acids in high yields and with an enantiomeric ratio higher than the epimeric ratio of the starting ketals; (b) the reaction solvent is water with the consequent economic and safety advantages; (c) no metal catalyst is required and (d) the optically active alpha-arylalkanoic acid is separated from the reaction mixture by simple filtration.

By considering the overall process for the preparation of optically active alpha-arylalkanoic acids according to the present invention it may be said that it consists of two quite new steps: the stereoselective halogenation of a ketal of formula A in which X is hydrogen and the enantioselective rearrangement of the thus obtained ketal of formula A in which X is a chlorine, bromine or iodine atom.

More specifically the overall process for the selective preparation of the S-enantiomer of an alpha-arylalkanoic acid according to the present invention consists thus of two quite new steps: the stereoselective halogenation of the suitable ketal of formula A in which X is hydrogen and in which the carbon atoms marked by an asterisk are both in the R configuration, to selectively obtain the epimer RRS of the ketal of formula A in which X is a chlorine, bromine or iodine atom and the enantioselective rearrangement of the thus obtained ketal in water under acidic conditions.

Such a process is possible thanks to the unexpected characteristics of the ketals of formula A shown both in the alpha halogenation step and in the aqueous rearrangement step.

The rearrangement method may be also performed in different less advantageous manners depending on the starting ketal. For example, the ketals of formula (A) in which X is a iodine atom, when Ar is the 6-methoxy-2-naphthyl group and R is a methyl, can be rearranged according to the procedure given in European patent application No. 89711, or by oxidation as described in Italian patent application No. 21841 A/82.

Likewise, the ketals of formula (A) in which X is any halogen atom can be rearranged in the presence of certain metal salts, as described in European patent application Nos. 34871 and 35305 and in J. Chem. Soc., Perkin I, 11, 2575 (1982), or in a protic polar medium in neutral or weakly alkaline conditions, optionally in the presence of an inert diluent, as described in Italian patent application No. 22760 A/82 or in European patent application No. 101,124.

The latter aforesaid method has important advantages relative in particular to its ease of industrial realization and to the fact that it does not require the presence of metal salts as catalysts. The aforesaid rearrangement reactions lead in general to the formation of alpha-arylalkanoic acids in the form of their derivative, in particular esters. These are then hydrolysed to the corresponding free acids by conventional methods.

Of the optically active alpha-arylalkanoic acids, the most important from the pharmacological viewpoint is 2-(6-methoxy-2-naphthyl)propionic acid, of which the S(+)isomer is known as Naproxen. In a specific embodiment, the present invention relates to compounds of formula

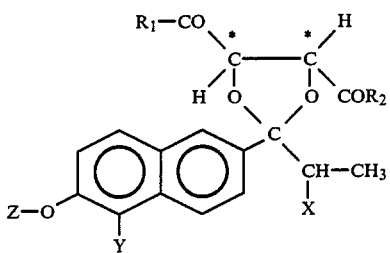

(B)

(in which $R_1$, $R_2$ and X have the meanings given for the formula (A), Y represents a hydrogen atom or a chlorine or bromine atom and Z represents a hydrogen atom, a methyl or an alkaline metal) and their use in the preparation of Naproxen by rearrangement.

The carbon atoms indicated with an asterisk have R configuration and when X is different from hydrogen, the carbon atom to which it is bonded has S configuration.

A compound of formula (B) in which X represents a halogen atom and Z a methyl, may be rearranged in the presence of certain metal salts such as Ag and Zn, or in a polar solvent under neutral or slightly alkaline conditions.

Moreover a compound of formula (B) in which Z represents an alkaline metal, may be rearranged in an aqueous or organic medium under neutral or alkaline conditions.

In any case the preferred embodiment according to the present invention is the rearrangement of the ketals of formula B (in which X=Cl, Br, I) in water, under acidic conditions.

The rearrangement of the epimer RRS of the ketals of formula B leads to S(+)-Naproxen or its direct precursors, for example containing Y substituent.

In preparing Naproxen, it is necessary to eliminate the substituent Y when this is a chlorine or bromine atom. This is done by hydrogenolysis either on the alpha-arylalkanoic acid or on the relative ester. The reaction involving rearrangement of the compounds of formula (A), in particular when conducted in a medium free from alcohols and glycols under mild conditions, can lead to the formation of new intermediate esters of formula

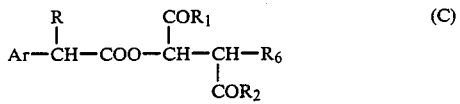

(C)

(in which Ar, R, $R_1$ and $R_2$ have the meanings given for formula A) and $R_6$ is OH, Cl, Br or I. Depending on the reaction conditions, $R_6$ can also assume other meanings such as acetate, propionate or benzoate.

Hydrolysis of the compounds of formula (C) then leads to the corresponding alpha-arylalkanoic acids.

Likewise, the rearrangement of the compounds of formula (B), when carried out in a medium free from alcohols and glycols, can lead to the production of intermediate esters of formula:

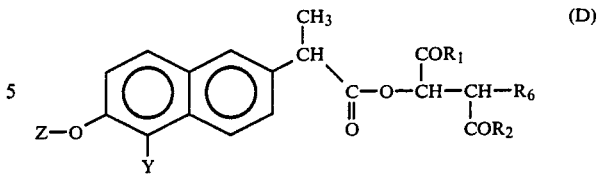

(D)

(in which $R_1$, $R_2$, $R_6$ and Y have the meanings given for formula (B), and Z represents a hydrogen atom or a methyl), which on hydrolysis form the alpha-arylalkanoic acid known as Naproxen or its immediate precursors. Again in this case, in which the transformation of the halogen ketals to aryl-alkanoic acids takes place in two stages, there is no substantial racemisation, and thus the desired optically active aryl-alkanoic acid is selectively and prevalently obtained. The compounds of formula (C) are new compounds which constitute a further object of the present invention, in that they have interesting properties which make them useful from various aspects. As already stated, the compounds of formula (C) form the corresponding alpha-arylalkanoic acids on hydrolysis.

Moreover, because of the presence of the two asymmetric carbon atoms in the alcoholic moiety (the atoms to which the $COR_1$ and $COR_2$ groups are bonded respectively), the esters of formula (C) are useful for the optical resolution of the alpha-arylalkanoic acids.

The resolution of an acid into its optical isomers is generally carried out by forming salts with an optically active base. The use of the compounds (C) constitutes a new process for the resolution of mixtures of optically active alpha-arylalkanoic acids by forming an ester with tartaric acid or one of its derivatives, instead of forming a salt with an optically active base.

The use of the compounds of formula (C) for resolving an alpha-arylalkanoic acid is particularly advantageous when, by means of the aforesaid process for rearranging the ketals (A), esters of formula (C) are obtained enriched in the desired isomer.

It is evident that the compounds of formula (C) are useful for the optical resolution of alpha-arylalkanoic acids independently from the method of preparation.

In this respect, it is possible to prepare the compounds of formula (C) by esterifying a racemic alpha-arylalkanoic acid (or one which is already rich in one of the two enantiomers) independently from how this has been prepared.

The compounds of formula (D), whether prepared by rearrangement of a compound of formula (B) or prepared by esterifying racemic 2-(6-methoxy-2-naphthyl)-propionic acid or one of its immediate precursors using tartaric acid or one of its derivatives, are useful for separating, by means of crystallization, the ester of formula (D) which on hydrolysis produces Naproxen in a substantially pure form.

A further unexpected property of the compounds of formula (C) is that they are in themselves pharmacologically active compounds. The compounds of formula (D) have proved particularly interesting. The following tables give the data relative to the anti-inflammatory and antipyretic activity of the compounds (D) in which:
$R_1=R_2=OCH_3$; $R_6=OH$; Y=H; $Z=CH_3$ (a)
$R_1=R_2=OCH_3$; $R_6=OH$; Y=Br; $Z=CH_3$ (b)
compared with Naproxen and with 5-Br Naproxen. (c)

From these data it is evident that the new considered compounds, although having a lesser activity than Naproxen, still have an interesting activity which could find practical application in human therapy under determined conditions.

TABLE 1
Anti-inflammatory activity of the derivatives (a) and (b) with respect to Naproxen and 5-bromo-Naproxen (c) by oral administration

| Compound | Dose μM/kg/os | Inhibition (after 3 h) % | ED$_{50}$ (L.C. 95%) |
|---|---|---|---|
| (a) | 10 | 0 | 175 |
|  | 30 | 0 | (110–280) |
|  | 100 | 16 |  |
| (b) | 10 | 3 | 160 |
|  | 30 | 14 | (100–250) |
|  | 100 | 20 |  |
| (c) | 10 | 6 |  |
|  | 30 | 34 |  |
|  | 100 | 34 | 196 |
|  | 300 | 56 | (120–304) |
| Naproxen | 10 | 38 |  |
|  | 30 | 45 | 31 |
|  | 100 | 66 | (19–49) |

TABLE 2
Antipyretic activity of compound (a) and (b) with respect to Naproxen and 5-bromo-Naproxen (c) by oral administration in rats

| Compound | Dose μM/kg/oral | Change in body temperature (°C.) after 1 hour | after 2 hours |
|---|---|---|---|
| a | 10 | −0.02 | +0.02 |
|  | 30 | +0.07 | −0.61 |
|  | 100 | +0.01 | −0.76 |
|  | 300 | +0.03 | −0.81 |
| b | 10 | −0.17 | −0.19 |
|  | 30 | −0.49 | −0.68 |
|  | 100 | −0.46 | −0.68 |
| c | 30 | −0.17 | −0.66 |
|  | 100 | −1.33 | −1.67 |
|  | 300 | −1.42 | −1.84 |
| Naproxen | 3 | −0.38 | −0.52 |
|  | 10 | −1.22 | −1.48 |
|  | 30 | −1.86 | −1.89 |

TABLE 3
Antipyretic activity of compounds (a) and (b) with respect to Naproxen and 5-bromo-Naproxen (c) by peritoneal administration in rats

| Compound | Dose μM/kg/oral | Change in body temperature (°C.) after 30 min | after 1 hour | after 4 hours |
|---|---|---|---|---|
| a | 10 | −0.26 | −0.52 | −0.19 |
|  | 30 | −0.61 | −1.02 | −0.56 |
| b | 10 | −0.24 | −0.52 | −0.26 |
|  | 30 | −0.77 | −0.87 | −0.44 |
| c | 30 | −0.55 | −1.01 | +0.06 |
|  | 100 | −0.78 | −1.45 | −0.99 |
| Naproxen | 10 | −1.00 | −1.10 | −0.86 |

Some pratical examples of the process according to the present invention are described hereinafter in order to illustrate the invention but without in any way limiting it.

EXAMPLE 1

Preparation of the compound 2-ethyl-2-(6-methoxy-2-naphthyl)-1,3-dioxolane-4(R),5(R)-dicarboxylic acid dimethyl ester.

1-(6-methoxy-2-naphthyl)-propan-1-one (46.5 g; 0.217 moles), L(+)tartaric acid dimethyl ester (300 g), trimethyl orthoformate (94 g; 0.887 moles) are gradually heated up to complete solution. Methanesulphonic acid (1.48 g; 0.0154 moles) is then added and the obtained solution is refluxed for 2 hours; it is cooled at room temperature and the reaction mixture is slowly added to a 10% solution of Na$_2$CO$_3$ (500 ml). It is extracted with methylene chloride and the organic extracts are repeatedly washed with water.

The organic phase is dried on Na$_2$SO$_4$ and the solvent is evaporated under reduced pressure.

The residue is crystallized from methanol (250 ml).

The desired product is obtained (51.68 g; 0.138 moles; yield 63.6%) having the following characteristics:

m.p.=73°–74° C.

$[\alpha]_D^{20}$ = +33.04 (c=1%, CHCl$_3$).

I.R. (Nujol): 1770, 1740 cm$^{-1}$ (stretching C=0).

NMR (CDCl$_3$-TMS, 200 MHz) δ (ppm): 0.94 (t, 3H, J=7,5 Hz); 2.08 (q, 2H, J=7,5 Hz); 3.46 (s, 3H); 3.84 (s, 3H); 3.90 (s, 3H); 4.86 (2H, ABq, Δν=10.80, J=6 Hz); 7.1–7.9 (m, 6H).

EXAMPLE 2

Preparation of the mixture of the diastereoisomers of 2-(1-bromoethyl)-2-(6-methoxy-2-naphthyl)-1,3-dioxolane-4(R),5(R)-dicarboxylic acid dimethylester.

To a solution of the compound obtained in Example 1 (37.4 g; 0.1 mole) in 1,2-dichloroethane (100 ml), tetra-n-butylammonium perbromide [N(n.C$_4$H$_9$)$_4$Br$_3$] (48.2 g; 0.1 mole) is added.

The reaction mixture is kept at 20° C. for 24 h and then slowly added under stirring to a 10% solution of Na$_2$CO$_3$ (200 ml). It is extracted with toluene (2×200 ml) and the combined organic extracts are washed with a 2% solution of NaHCO$_3$ (3×100 ml). The organic phase is dried on Na$_2$SO$_4$ and the solvent evaporated under reduced pressure. The crude product obtained (48 g) is purified by chromatography on a silica gel column (eluent hexene:diethylether=75:25) to give 13 g of the desired mixture of diastereoisomers.

The ratio between the two diastereoisomers (1:2) determined by $^1$H-NMR (200 MHz) is 7:3.

Diastereoisomer 1 (RRS): $^1$H-NMR (CDCl$_3$-TMS), δ (ppm): 1.68 (d, 3H, J=7.5 Hz); 3.54 (s, 3H); 3.90 (s, 3H); 4.08 (s, 3H); 4.48 (q, 1H, J=7.5 Hz); 4.94 (2H, ABq, Δν=26.8; J=7.2 Hz); 7.1–8.0 (6H, m).

Diastereoisomer 2 (RRR)

$^1$H-NMR (CDCl$_3$-TMS), δ (ppm): 1.64 (d, 3H, J=7.5 Hz); 3.58 (s, 3H); 3.89 (s, 3H); 4.08 (s, 3H); 4.50 (q, 1H, J=7.5 Hz); 4.89 (2H, Abq, Δν=36.3, J=6.3 Hz); 7.1–8.0 (6H, m).

EXAMPLE 3

Preparazione of the 2(R)-hydroxy-3(R)-[2-(6-methoxy-2-naphthyl)propanoyl]-butanedioic acid dimethyl ester.

A mixture of diastereoisomers 1:2=67:33, obtained according to example 2 (5 g; 0.011 moles) dissolved into CH$_2$Cl$_2$ (61 ml) and kept at 0° C. under inert atmosphere is added with silver tetrafluoroborate (2.33 g; 0.012 moles). The reaction mixture is kept at 0° C. for 30 minutes and then the temperature is allowed to raise up to room temperature.

The mixture is filtered and the precipitate washed with CH$_2$Cl$_2$. The organic phases are washed with water and dried on Na$_2$SO$_4$.

The solvent is evaporated under reduced pressure to give a mixture of diastereoisomeric esters (ratio determined by NMR, 200 MHz, A:B=64:36).

$^1$H-NMR (CDCl$_3$-TMS), δ, (ppm-):

Diastereoisomer A (RRS): 1.62 (d, 3H, J=8 Hz); 3.22 (s, 3H); 3.83 (s, 3H); 3.92 (s, 3H), 3.21 (d, 1H, J=7.2 Hz);

3.95 (q, 1H, J=8 Hz); 4.68 (dd, 1H, $J_{CH-OH}$=7.2 Hz, $J_{CH-CH}$=2.47 Hz); 5.37 (d, 1H, J=2.47 Hz); 7.1–7.8 (6H, aromatic protons).

Diastereoisomer B (RRR): 1.66 (d, 3H, J=8 Hz); 3.58 (s, 3H); 3.72 (s, 3H); 3.92 (s, 3H); 3.24 (d, 1H, J=7.6 Hz); 3.97 (q, 1H, J=8 Hz), 4.78 (dd, 1H, $J_{CH-OH}$=7.6 Hz, $J_{CH-CH}$=2.47 Hz); 5.45 (d, 1H, J=2.47 Hz); 7.1–7.8 (6H, aromatic protons).

EXAMPLE 4

Preparation of 2-(6-methoxy-2-naphthyl)propionic acid.

A mixture of diastereoisomer esters A and B prepared as described in Example 3 (ratio A:B=62:38) (3.2 g) dimethoxyethane (24 ml), hydrochloric acid 12N (24 ml) is kept under stirring, at 95° C. for 2.5 h. It is cooled to room temperature, poured into water and extracted with $CH_2Cl_2$.

The combined organic extracts are washed with a saturated solution of sodium bicarbonate.

The aqueous phase is acidified to give the 2-(6-methoxy-2-naphthyl)propionic acid (1.3 g).

An analitically pure sample obtained by column chromatography on silica gel (eluent hexane:diethylether=1:1), with $[\alpha]_D^{20}$=+12.9° (c=1%, $CHCl_3$) is esterified with diazomethane.

The obtained methyl ester is analyzed by $^1H$-NMR (200 MHz) using an optically active shift agent (Europium (III)-tris-[3-(eptafluoropropylhydroxymethylene)-d-camphorate] in $CDCl_3$).

The enantiomeric ratio is (+)S:(−)R=62:38.

EXAMPLE 5

Preparation of the 2-(6-methoxy-2-naphthyl)-propionic acid.

A mixture of diastereoisomeric ketals prepared as described in Example 2, in a ratio of 1:2=67:33, is heated at 125° C. in ethylene glycol, in the presence of potassium acetate for 20 h. After work up of the reaction mixture, a mixture of esters is obtained that are hydrolyzed as described in Example 4. The (+)(S)-2-(6-methoxy-2-naphthyl)propionic acid (Naproxen) is obtained, with an optical purity of 40%; m.p.=151°–152° C.

EXAMPLE 6

Preparation of the diastereoisomeric mixture of the compound 2-(1-bromoethyl)-2-(5-bromo-6-methoxy-2-naphthyl)-1,3-dioxolane-4(R),5(R)-dicarboxylic acid dimethyl ester.

To a solution of 2-ethyl-2-(6-methoxy-2-naphthyl)-1,3-dioxolane-4(R),5(R)-dicarboxylic acid dimethyl ester (3.74 g; 0.01 moles) in $CCl_4$ (70 ml) kept at 0° C. under inert atmosphere, a solution of bromine (3.2 g; 0.02 moles) in $CCl_4$ (7 ml) cooled at 0° C. is added dropwise in 1 h.

The mixture is kept at 0° C. for two hours, then poured under vigorous stirring into an 10% aqueous solution of $Na_2CO_3$ (250 ml) and extracted with $CH_2Cl_2$ (3×50 ml).

The combined organic extracts are dried on $Na_2SO_4$ and the solvent evaporated under vacuum. The residue (5 g; 0.0093 moles; yield 93%) consists of a mixture of the two diastereoisomers identified with 3 and 4.

The ratio between the diastereoisomers 3:4, determined by HPLC and $^1H$-NMR, is 95:5.

The major isomer has the same configuration (S) of the diastereoisomer 1 described in Example 2, referring to the aliphatic carbon atom bonded to bromine.

Diastereoisomer 3 (RRS): $^1H$-NMR (200 MHz) ($CDCl_3$-TMS), δ (ppm): 1.66 (d, 3H, J=6.8 Hz); 3.52 (s, 3H); 3.88 (s, 3H); 4.05 (s, 3H); 4.46 (q, 1H, J=6.8 Hz); 4.94 (2H, ABq, J=6 Hz); 7.28–8.24 (5H, aromatic protons).

Diastereoisomer 4 (RRR): $^1H$-NMR (200 MHz) ($CDCl_3$-TMS), δ (ppm): 1.63 (d, 3H, J=6.8 Hz); 3.56 (s, 3H); 3.87 (s, 3H); 4.05 (s, 3H); 4.48 (q, 1H, J=6.8 Hz); 4.91 (2H, ABq, J=6 Hz); 7.28–8.24 (5H, aromatic protons).

The HPLC analysis (high pressure liquid chromatography) has been performed under the following conditions:

Hewlett Packard instrument mod. 1084/B with variable wavelength UV detector:
Analytical conditions:
Column BRAWNLEE LABS RP8 (5μ) spheri 250 mm×4.6 mm (internal diameter)
Solvent A: bidistilled water, flow 0.9 ml/min
Solvent B: methanol, flow 1.1 ml/min
Solvent A temperature: 60° C.
Solvent B temperature: 40° C.
Column temperature: 50° C.
Wavelength (λ): 254 nanometers
Injection: 10 μl of a solution containing 3 mg/ml of a sample in acetonitrile.
Retention times:
Diastereoisomer 3: 18.20 min
Diastereoisomer 4: 19.90 min A mixture of diastereoisomers 3 and 4 in ratio 95:5 obtained as above described is chromatographed on silica gel, by using as eluent a mixture of diethylether:hexane=3:7.

The collected fractions are separately analyzed by HPLC. The fractions containing the diastereoisomer 3 showing a diastereoisomeric purity higher than 99% are collected.

The solvent is evaporated under vacuum to give the pure diastereoisomer 3.

$^1H$-NMR (200 MHz) ($CDCl_3$-TMS) delta (ppm): 1.66 (d, 3H, J=7.5 Hz); 3.52 (s, 3H); 3.88 (s, 3H); 4.05 (s, 3H); 4.46 (q, 1H, J=7.5 Hz); 4.94 (2H, ABq, J=7.2 Hz); 7.28–8.24 (5H, aromatic protons).

EXAMPLE 7

Preparation of a mixture of diastereoisomers of the compound 2-(1-bromoethyl)-2-(5-bromo-6-methoxy-2-naphthyl)-1,3-dioxolane-4(R),5(R)-dicarboxylic acid dimethyl ester.

The reaction described in Example 6 has been repeated with different solvents and at different temperatures according to the following procedure.

To a solution of 2-ethyl-2-(6-methoxy-2-naphthyl)-1,3-dioxolane-4(R),5(R)-dicarboxylic acid dimethyl ester (0.01 moles) in the solvent indicated in the following Table (70 ml), kept under inert atmosphere at the temperature also indicated in the Table, a solution of bromine (0.02 moles) in the same solvent (7.0 ml), precooled to the temperature of the above mixture, is added. The so obtained reaction mixture is kept at the temperature indicated to reach a substantially complete conversion. It is then worked up as described in Example 6. The ratio between the diastereoisomers 3 and 4 is indicated in the Table.

TABLE

| Solvent | T (°C.) | Ratio diast. 3 / diast. 4 |
|---|---|---|
| Carbon tetrachloride | 20 | 93/7 |
| 1,2-Dichloroethane | 20 | 93/7 |
| 1,2-Dichloroethane | 0 | 91/9 |
| 1,2-Dichloroethane | −30 | 92/8 |
| 1,1,2,2-Tetrachloroethane | 20 | 89/11 |
| Chlorobenzene | 20 | 90/10 |
| Benzene | 20 | 91/9 |
| Benzene | 0 | 92/8 |
| Toluene | 20 | 91/9 |
| Ethylenglycoldimethylether | 20 | 86/14 |
| Acetonitrile | 20 | 82/18 |
| Cyclohexane | 20 | 88/12 |
| Orthodichlorobenzene | 20 | 89.2/10.8 |
| Sulfolane | 27 | 78/22 |
| Ethylacetate | 20 | 91/9 |
| Para-dichlorobenzene | 60 | 87/13 |
| Carbondisulfide | 15 | 92.3/7.7 |
| Acetic acid | 15 | 89/11 |
| Hexafluorobenzene | 15 | 90.3/9.7 |
| Molar yield 90–95% | | |

EXAMPLE 8

Preparation of 2-(1-bromoethyl)-2-(5-bromo-6-methoxy-2-naphthyl)-1,3-dioxolane-4(R), 5(R)-dicarboxylic acid dimethylester.

To a solution of 2-ethyl-2-(6-methoxy-2-maphthyl)-1,3-dioxolane-4(R), 5(R)-dicarboxylic acid dimethyl ester (70 g; 0.187 moles) in 1,2-dichloroethane (175 ml) kept at −30° C., under inert atmosphere and under stirring, a bromine solution (59.8 g; 0.374 moles) in 1,2-dichloroethane (140 ml) is added in 2 h.

The reaction mixture is kept at −30° C. up to a complete conversion of the starting product, then is added slowly dropwise to a 10% solution of $Na_2CO_3$ (1000 ml) under vigorous stirring.

The organic phase is separated, washed with water, dried on $Na_2SO_4$ and the solvent evaporated under vacuum. The mixture of the two diastereoisomers 3:4 is obtained in a ratio 9:1. The above ratio has been determined by HPLC and $^1H$-NMR.

EXAMPLE 9

Preparation of 2(R)-hydroxy-3(R)-[2-(5-bromo-6-methoxy-2-naphthyl)propanoyl]-butanedioic acid dimethylester.

To a solution of 2-(1-bromoethyl)-2-(5-bromo-6-methoxy-2-naphtyl)-1,3-dioxolane-4(R), 5(R)-dicarboxylic acid dimethyl ester (2.66 g; 0.005 moles; ratio diastereoisomer 3 to diastereoisomer 4 = 85:15 determined by HPLC) in 1,2-dichloroethane (20 ml), kept under stirring at −15° C. under inert atmosphere, silver tetrafluoroborate (1.17 g 0.006 moles) is added.

The reaction mixture is kept at −15° C. for 2 h, then allowed to reach room temperature in about 1 h and filtered. The organic phase is washed with water, dried on $Na_2SO_4$ and the solvent evaporated under vacuum.

The desired product is obtained (2.2 g; 0.0047 moles; yield 94%) as a mixture of two diastereoisomers named C and D, in a ratio C:D=84:16 determined by $^1H$-NMR, 200 MHz.

$^1H$-NMR (CDCl$_3$-TMS).

Diastereoisomer C (RRS)—The data are consisting with the given structure; the data which refer to the aliphatic part are analogous to those of the diastereoisomer A described in Example 3.

Diastereoisomer D (RRR)—The data are quite consisting with the given structure; the data which refer to the aliphatic part are analogous to those of diastereoisomer B described in Example 3.

The diastereoisomer C has been separated in pure form by crystallization from methanol. M.p.=124°–126° C.; $[\alpha]_D^{20}$ = +60.2 (c=1% in CHCl$_3$).

EXAMPLE 10

Preparation of S(+)-2-(5-bromo-6-methoxy-2-naphthyl)-propionic acid.

(a) a mixture of:

2(R)-hydroxy-3(R)-[2-(5-bromo-6-methoxy-2-naphthyl-propanoyl)]butanedioic acid dimethyl ester (diastereoisomer C of Example 9; 0.5 g; 1.065 mmoles)

sodium hydroxide (0.170 g; 4.26 mmoles)

water (2.5 ml)

methanol (3.5 ml)

is kept under stirring at room temperature for 18 hours. The mixture is diluted with water and extracted with dichloromethane. The aqueous phase is acidified with conc. HCl and extracted with dichloromethane.

The organic phase is then washed with water, dried and the solvent evaporated under vacuum. The so obtained crude acid is purified by chromatography on silica gel (eluent hexene:diethylether=8:2).

The S(+)-2-(5-bromo-6-methoxy-2-naphthyl)-propionic in the pure form is obtained; m.p.=155°–157° C.; $[\alpha]_{578}^{20}$ = +20.5 (c=0.5% in CHCl$_3$). Starting from this acid, by debromination according to the method described in the Belgian Patent No. 892.689, Naproxen is obtained having the same optical purity of the starting 5-Bromo derivative.

(b) a mixture of:

2(R)-hydroxy-3(R)-[2-(5-bromo-6-methoxy-2-naphthyl)-propanoyl]-butanedioic acid dimethyl ester (diastereoisomer C obtained according to Example 9; 0.2 g; 0.426 mmoles).

1,2-dimethoxy-ethane (3 ml)

conc. HCl (3 ml)

is kept at 95° C. for 2 h. The reaction mixture is then cooled to room temperature, diluted with water and extracted with $CH_2Cl_2$. The organic phase is washed with water and extracted with 10% sodium bicarbonate.

The basic aqueous extract is acidified with conc.HCl and extracted with $CH_2Cl_2$.

The organic extract is washed with water, dried on $Na_2SO_4$ and the solvent evaporated under reduced pressure.

The optically pure S(+)-2-(5-bromo-6-methoxy-2-naphthyl)-propionic acid is obtained:

$[\alpha]_{578}^{20}$ = +44.9 (c=0.5% in CHCl$_3$).

This acid is debrominated to give Naproxen the same optical purity, following the procedure described in the Belgian Patent No. 892.689: $[\alpha]_D^{20}$ = +66° (c=1% in CHCl$_3$).

EXAMPLE 11

Preparation of the 2-(5-bromo-6-methoxy-2-naphthyl)propionic acid.

A mixture of 2-(1-bromoethyl)-2-(5-bromo-6-methoxy-2-naphthyl)-1,3-dioxolane-4(R), 5(R)-dicarboxylic acid dimethyl ester prepared according to Example 8 (2.66 g; 5 mmoles; diaster.3:diaster.4=9:1 as determined by HPLC), sodium bicarbonate (1.7 g; 20 mmole) and water is refluxed for 22 h. The reaction mixture is cooled to room temperature and extracted with diethylether. The aqueous phase is acidified with conc.HCl and the precipitate filtered and washed with water.

The so obtained crude acid (1.13 g) is purified on a silica gel column (eluent hexane:diethylether in ratio 8:2).

The 2-(5-bromo-6-methoxy-2-naphthyl)-propionic acid (0.92 g; 3 mmoles; yield 60%) is obtained—m.p.=156°–158° C.; $[\alpha]_{578}^{20}$=+23.5 (c=0.5% in CHCl$_3$).

EXAMPLE 12

Preparation of 2-ethyl-2-(6-methoxy-2-naphthyl)-1,3-dioxolane-4(R), 5(R)-dicarboxylic acid diethyl ester.

1-(6-methoxy-2-naphthyl)-propan-1-one (20.0 g; 0.093 moles), diethyl ester of L(+)tartaric acid (160 g) and triethyl orthoformate (37 g; 0.25 moles) are slowly heated up to complete solution.

Methanesulphonic acid (0.68 g; 0.007 moles) is added and the solution is refluxed for 1 h.

The reaction mixture is cooled to room temperature and added to a 10% solution of Na$_2$CO$_3$ (250 ml) under vigorous stirring. It is extracted with CH$_2$Cl$_2$ and the organic extracts are repeatedly washed with water.

The organic phase is dried on Na$_2$SO$_4$ and the solvent is evaportated under reduced pressure.

The crude product is gradually heated up to 180° C. (external bath) under a pressure of 0.1 mmHg.

The desired product is obtained (33.6 g; 0.084 moles; yield 90%) having the following characteristics:

$[\alpha]_D^{20}$=+20.59° (c=1%, CHCl$_3$).

I.R. (NEAT): 1770, 1740 cm$^{-1}$ (stretching C=O).

$^1$H-NMR (CDCl$_3$-TMS) δ (ppm): 0.95 (t, 3H, J=6.4 Hz); 1.02 (t, 3H, J=7.3 Hz); 1.3 (t, 3H, J=7.3 Hz); 2.08 (q, 2H, J=6.4 Hz); 3.9 (s, 3H); 3.88 (dq, 2H, J=11 Hz, J=7.3 Hz); 4.30 (q, 2H, J=7.3 Hz); 4.82 (ABq, 2H, J=5.94 Hz); 7–8 (6H, aromatic protons).

EXAMPLE 13

Preparation of the diastereoisomers mixture of 2-(1-bromoethyl)-2-(5-bromo-6-methoxy-2-naphthyl)-1,3-dioxolane-4(R), 5(R)-dicarboxylic acid diethyl ester.

To a solution of 2-ethyl-2-(6-methoxy-2-naphthyl)-1,3-dioxolane-4(R), 5(R)-dicarboxylic acid diethyl ester (2 g; 0.005 moles) in CCl$_4$ (35 ml) is added a solution of bromine (1.6 g; 0.01 moles) in CCl$_4$ (3.5 ml), under inert atmosphere, at 20° C.

The mixture is kept at 20° C. for two hours and then worked up as described in Example 6.

The desired diastereoisomeric mixture is obtained (named as 5 and 6) in 93% yield.

The ratio between the diastereoisomers, determined by HPLC, is 5:6=91.5:8.5.

The diastereoisomer 5 (which is the prevalent one) shows the same configuration (S) of the diastereoisomer 1 (Example 2) and of diastereoisomer 3 (Example 6) with respect to the aliphatic carbon atom bonded to bromine.

$^1$H-NMR (CDCl$_3$-TMS) (200 MHz).

Diastereoisomer 5 (RRS): δ (ppm) 1.04 (t, 3H, J=7 Hz); 1.31 (t, 3H, J=7 Hz); 1.65 (d, 3H, J=6.8 Hz); 3.92 (dq, 2H, J=11.3 Hz, J=7 Hz); 3.98 (s, 3 H); 4.3 (q, 2H, J=7 Hz); 4.48 (q, 1H, J=6.8 Hz); 4.88 (ABq, 2H, J=6.5 Hz); 7.2–8.2 (5H, aromatic protons).

Diastereoisomer 6 (RRR): δ (ppm) 1.09 (t, 3H, J=7 Hz); 1.29 (t, 3H, J=7 Hz); 1.62 (d, 3H, J=6.8 Hz); 3.98 (s, 3H); 4.29 (q, 2H, J=7 Hz); 4.85 (ABq, 2H, J=6.5 Hz); 7.2–8.2 (5H, aromatic protons).

HPLC analysis performed under essentially the same conditions as described in Example 6, with the only difference that the percentage of the solvent B is 58% (total flow 2 ml/min).

Diastereoisomer 5: retention time 24.03 minutes
Diastereoisomer 6: retention time 25.00 minutes.

EXAMPLE 14

Preparation of 2-ethyl-2-(6-methoxy-2-naphthyl)-1,3-dioxolane-4(R), 5(R)-dicarboxylic acid A mixture of 2-ethyl-2-(6-methoxy-2-naphthyl) 1,3-dioxolane-4(R), 5(R)-dicarboxylic acid dimethyl ester (4.68 g; 12.5 mmoles), NaOH (1 g, 25 mmoles) and water (50 ml) is kept under stirring at room temperature for 5 h.

The reaction mixture is filtered and the aqueous phase acidified with conc. HCl to pH 1.

It is then extracted with diethylether and the combined organic extracts are washed with water and dried on Na$_2$SO$_4$. Evaporation of the solvent under vacuum gives 2-ethyl-2-(-methoxy-2-naphthyl)-1,3-dioxolane-4(R), 5(R)-dicarboxylic acid (3.46 g; 10 mmoles); yield 80%), m.p.=100°–102° C.

$^1$H NMR (200 MHz) (CDCl$_3$-TMS) delta (ppm): 0.92 (t, 3H, J=7 Hz); 2.07 (q, 2H, J=7 Hz); 3.86 (s, 3H); 4.78 (2H, ABq, Δν=4.2; J=5.8 Hz); 7,0–8,0 (6H, aromatic protons).

A sample esterified with diazomethane in diethylether gives the starting methyl ester with unchanged $^1$HNMR, I.R., m.p., and $[\alpha]$.

EXAMPLE 15

Preparation of 2-(1-bromoethyl)-2-(5-bromo-6-methoxy-2-naphthyl)-1,3-dioxolane-4(R), 5(R)-dicarboxylic acid.

A mixture consisting of the two diastereoisomers of 2-(1-bromo-ethyl)-2-(5-bromo-6-methoxy-2-naphthyl)-1,3-dioxolane-4(R), 5(R)-dicarboxylic acid dimethyl ester, in ratio 9:1 (6.65 g; 12.5 mmoles), NaOH (1 g; 25 mmoles), dimethoxyethane (10 ml) and water (10 ml) is kept under stirring at room temperature for 2 h.

The reaction mixture is diluted with water and extracted with diethylether.

The aqueous phase is then acidified to pH 1 with conc. HCl and extracted with diethylether.

The combined organic extracts are washed with water and dried on Na$_2$SO$_4$.

The evaporation of the solvent under vacuum leads to the two diastereoisomers of 2-(1-bromoethyl)-2-(5-bromo-6-methoxy-2-naphthyl)-1,3-dioxolane-4(R), 5(R)-dicarboxylic acid (5.8 g; 11.5 mmoles; yield 92%) named with the numbers 7 and 8. The ratio between the diastereoisomers 7 and 8, determined by $^1$HNMR (200 MHz), is of 9:1.

Diastereoisomer 7 (RRS) (CDCl$_3$-TMS) delta (ppm): 1.60 (d, 3H, J=7 Hz); 4.00 (s, 3H); 4.49 (q, 1H, J=7 Hz); 4.87 (2H, ABq, Δν=18.9; J=6.5 Hz); 7.2–8.2 (5H, aromatic protons).

EXAMPLE 16

Preparation of 2-(1-bromoethyl)-2-(5-bromo-6-methoxy-2-naphthyl)-1,3-dioxolane-4(R), 5(R)-dicarboxylic acid.

A mixture of 2-[1(S)bromoethyl]-2-(5-bromo-6-methoxy-2-naphthyl)-1,3-dioxolane-4(R), 5(R)-dicarboxylic acid dimethyl ester (diastereoisomer 3 in the pure form; 6.65 g; 12.5 mmoles), NaOH (1 g; 25 mmoles), dimethoxyethane (10 ml) and water (10 ml) is kept under stirring at room temperature for 2 h.

The reaction mixture is diluted with water and extracted with diethylether. Then the aqueous phase is acidified at pH 1 with conc. HCl and extracted with diethylether.

The combined organic extracts are washed with water and dried on $Na_2SO_4$.

Evaporating of the solvent under vacuum gives 2-[1(S)-bromoethyl]-2-(5-bromo-6-methoxy-2-naphtyl)-1,3-dioxolane-4(R), 5(R)-dicarboxylic acid (diastereoisomer 7).

$^1$H NMR (200 MHz) (CDCl$_3$-TMS) delta (ppm): 1.60 (d, 3H, J=7 Hz); 4.00 (s, 3H); 4.49 (q, 1H, J=7 Hz); 4.87 (2H, ABq, $\Delta\nu$=b 18.9; J=6 Hz); 7.2–8.2 (5 H, aromatic protons).

EXAMPLE 17

Preparation of 2(R)-hydroxy-3(R)-[2-(5-bromo-6-methoxy-2-naphthyl)propanoil]-butanedioic acid dimethyl ester.

To a mixture of the diastereoisomers 3 and 4 in ratio 94:6 (determined by HPLC) (10.0 g; 0.0188 moles) in 1,2-dichloroethane (75 ml) kept under stirring at +15° C., under inert atmosphere, a solution of silver tetrafluoborate (4.4 g; 0.0226 moles) in 1,2-dichloroethane (30 ml), is added in 15 min.

The reaction mixture is kept at +15° C. for 7 h, poured slowly into cooled water (100 ml) in such a manner that the temperature does not overcome +10° C.

The mixture is then filtered on Celite and the filtrate washed with $CH_2Cl_2$ (100 ml).

The organic phase is washed with water (2×200 ml) and dried on $Na_2SO_4$. Evaporating of the solvent under reduced pressure gives a residue (7.2 g; 0.0154 moles; yield 82%) consisting of a mixture of diastereoisomeric esters (ratio diast. C:D=91:9, determined by $^1$H NMR analysis).

EXAMPLE 18

Preparation of the compound 2-ethyl-2-(6-methoxy-2-naphthyl)-1,3-dioxolane-4(R), 5(R)-dicarboxylic acid diisopropyl ester.

1-(6-methoxy-2-naphthyl)-propan-1-one (10.3 g; 0.048 moles), di-isopropyl ester of L(+) tartaric acid (94 g) and trimethyl orthoformate (7.57 g; 0.071 moles), are gradually heated up to complete solution.

It is then added methanesulphonic acid (0.37 g; 0.0039 moles) and the solution is refluxed for 2.5 h (temperature of the solution 90° C). The reaction mixture is cooled and slowly added to a 10% solution of $Na_2CO_3$ (100 ml), under vigorous stirring.

It is extracted with $CH_2Cl_2$ and the organic extracts are washed with water (100 ml).

The organic phase is dried on $Na_2SO_4$ and the solvent is evaporated under reduced pressure to give 94 g of crude product.

The crude product is then slowly heated up to 220° C. (external bath) at 0.2–0.3 mm/Hg. The residue is purified by cromatography on a silica gel column (eluent hexene:diethylether=85:15) 2-ethyl-2(6-methoxy-2-naphthyl)-1,3-dioxolane-4(R), 5(R) dicarboxylic acid diisopropylester (14.2 g; 0.033 moles; yield 69%) was obtained.

I.R. (Neat): 1770, 1740 cm$^{-1}$ (stretching C=0).

$^1$H NMR (CDCl$_3$-TMS) (200 MHz) delta (ppm): 0.95 (t, 3H, J=7.6 Hz); 0.96 (d, 3H, J=6.4 Hz); 1.05 (d, 3H, J=6.4 Hz); 1.29 (d, 6H, J=6.4 Hz); 3.8 (s, 3H); 4.75 (ABq, 2H, J=6.6 Hz); 4.79 (q, 1H, J=6.4 Hz); 3.8 (s, 3H); 4.75 (ABq, 2H, J=6.6 Hz); 4.79 (q, 1H, J=6.4); 5.14 (ept., 1H, J=6.4); 7–8 (m, 6H).

EXAMPLE 19

Preparation of the diastereoisomeric mixture of the 2-(1-bromoethyl)-2-(5-bromo-6-methoxy-2-naphtyl)-1,3-dioxolane-4(R), 5(R)-dicarboxylic acid diisopropylester.

A solution of bromine (1.6 g; 0.01 moles) in CCl$_4$(3.5 ml) is added dropwise, at 15° C., under inert atmosphere, in 1 h to a solution of 2-ethyl-2-(6-methoxy-2-naphthyl)-1,3-dioxolane-4(R), 5(R)-dicarboxylic acid diisopropyl ester (2.15 g; 0.005 moles) in CCl$_4$ (35 ml). The mixture is kept at 15° C. for 2 h and then worked up as described in example 6.

The desired diastereoisomers mixture (isomeric 9 and 10) is obtained in a 94% yield.

The ratio between the two diastereoisomers as determined by HPLC is 9:10=93.9:6.1. $^1$H NMR (CDCl$_3$-TMS) (200 MHz).

Diastereoisomer 9 (RRS): delta (ppm): 0.96 (d, 3H, J=6.4 Hz); 1.06 (d, 3H, J=6.4 Hz); 1.3 (d, 6H, J=6.4 Hz); 1.67 (d, 3H, J=7.2 Hz); 3.98 (s, 3H); 4.47 (q, 1H, J=7.2 Hz); 4.80 (ABq, 2H, J=6.6 Hz); 4.80 (m, 1H, J=6.4 Hz); 5.15 (m, 1H, J=6.4 Hz); 7.2–8.2 (5H, aromatic protons).

Diastereoisomer 10 (RRS): delta (ppm): 0.96 (d, 3H, J=6.4 Hz); 1.06 (d, 3H, J=6.4 Hz); 1.28 (d, 6H, J=6.4Hz); 1.63 (d, 3H, J=7.2 Hz); 3.98 (s, 3H); 4.47 (q, 1H, J=7.2 Hz); 4.80 (ABq, 2H, J=6.6 Hz); 4.80 (m, 1H, J=6.4 Hz); 5.15 (m, 1H, J=6.4 Hz); 7.2–8.2 (5H, aromatic protons).

HPLC analysis performed as described in ex. 6, with the only difference that the percentage of solvent B is 62.5% (total flow 2 ml/min.)

Diastereoisomer 9: retention time 23.68 min.

Diastereoisomer 10: retention time 24.46 min.

EXAMPLE 20

Preparation of 2(R)hydroxy-3(R)-[2-(5-bromo-6-methoxy-2-naphthyl)propanoyl]-butanedioic acid diisopropylester.

Following the procedure described in ex. 17 a mixture of diastereouisomeric ketals 9 and 10 (ex. 19) in a ratio 9:10=94:6 determined by HPLC (2.0 g; 3.4 mmoles), a residue is obtained (1.6 g) that after purification by chromatography on silica gel column (eluent hexene:diethylether=1:1) gives a mixture of diastereiosomers esters (E and F) in ratio 90:10 (determined by $^1$H NMR (200 MHz) analysis).

$^1$H-NMR (CDCl$_3$-TMS) (200 MHz).

Diastereoisomer E (RRS): delta (ppm): 0.55 (d, 3H, J=6.12 Hz); 1.02 (d, 3H, J=6.12 Hz); 1.24 (d, 3H, J=6.12 Hz); 1.27 (d, 3H, J=6.12 Hz); 1.61 (d, 3H, J=7 Hz); 3.17 (d, 1H, J=6.8 Hz); 4.00 (q, 1H, J=7 Hz); 4.02 (s, 3H); 4.52 (ept, 1H, J=6.12 Hz); 4.62 (dd, 1H, J$_{CH-CH}$=2.2 Hz, J$_{CH-OH}$=6.8 Hz); 5.13 (ept, 1H, J=6.12 Hz); 5.30 (d, 1H, J=2.2 Hz); 7.2–8.2 (5H, aromatic system).

Diastereoisomer F (RRR): delta (ppm): 0.95 (d, 3H, J=6.12 Hz); 1.12 (d, 3H, J=6.12 Hz); 1.14 (d, 3H, J=3.12 Hz); 1.19 (d, 3H, J=6.12 Hz); 1.62 (d, 3H, J=7 Hz); 3.17 (d, 1H, J=6.8 Hz); 4.00 (q, 1H, J=7 Hz); 4.02 (s, 3H); 4.52 (ept, 1H, J=6.12 Hz); 4.62 (dd, 1H, J$_{CH-CH}$=2.2 Hz, J$_{CH}$.OH=6.8 Hz); 5.13 (ept, 1H, J=6.12

Hz); 5.41 (d, 1H, J=2.2 Hz); 7.2–8.2 (5H, aromatic system).

EXAMPLE 21

Preparation of the 2-(5-bromo-6-methoxy-2-naphthyl)-propionic acid.

A mixture of diastereoisomers E and F (ex. 20) in a ration E:F=90:10 (0.35 g; 0.648 mmoles), dimethoxyethane (4.6 ml) and 12N HCl (4.6 ml) is kept at 88° C. under stirring for 2 h. It is cooled to room temperature and then it is worked up as described in ex. 10(b).

The so obtained crude product is eluted through a silica gel column (eluent hexene:ethyl ether=8:2), to give the 2-(5-bromo-6-methoxy-2-naphthyl)propionic acid: m.p.=148–151° C.; $[\alpha]_{578}^{20}=+38°$ (c=0.5% CHCl$_3$).

The methylester of the above acid obtained by esterification with diazomethane, analyzed by $^1$H-NMR (200 MHz) using optically active shift agent (europium (III) tris-[3-(eptafluoropropylhydroxymethylene)-d-camphorate] in CDCl$_3$, shows a ratio between the enantiomers of S(+):R(−)=90:10.

EXAMPLE 22

Preparation of 2(R)hydroxy-3(R)-[2-(5-bromo-6-methoxy-2-naphthyl)propanoyl]-butanedioic acid diethylester.

Following the procedure as described in ex. 17 a mixture of diastereoisomeric ketals 5 and 6 (ex. 13) having a ratio 5:6=93:7, determined by HPLC, (2.41 g; 4.3 mmoles), a residue is obtained (1.95 g) that by elution through a silica gel column (eluent hexane:diethylether=1:1) gives a mixture of diastereoisomeric esters named as G and H (1.77 g; 3.6 mmoles; yield 83%) in ratio G:H=86:14 determined by $^1$H-NMR, 200 MHz.

$^1$H-NMR (CDCl$_3$-TMS) (200 MHz):

Diastereoisomer G (RRS): delta (ppm): 0.76 (t, 3H, J=7.2 Hz); 1.27 (t, 3H, J=7.2 Hz); 1.58 (d, 3H, J=7 Hz); 3.10 (d, 1H, J=7.12 H); 3.58 (q di AB, 2H, J$_{gem}$=12 Hz, J=7.2 Hz); 4 (q, 1H, J=7 Hz); 4.01 (s, 3H); 4.27 (q, 2H, J=7.2 Hz); 4.65 (dd, 1H, J$_{CH-OH}$=7.12 Hz); J$_{CH-OH}$=2.4 Hz); 5.32 (d, 1H, J=2.4 Hz); 7.2–8.2 (5H, aromatic protons).

Diastereoisomer H (RRR): delta (ppm): 1.08 (t, 3H, J=7.2 Hz); 1.14 (t, 3H, J=7.2 Hz); 1.62 (d, 3H, J=7 Hz); 3.1 (d, 1H, J=7.12 Hz); 3.58 (q di AB, 2H, Jgem=12 Hz, J=7.2 Hz); 4.00 (q, 1H, J=7Hz) 4.01 (s, 3H); 4.27 (q, 2H, J=7.2 Hz); 4.65 (dd, 1H, J$_{CH-OH}$=7.12 Hz; J$_{CH-CH}$=2.4 Hz); 5.44 (d, 1H, J=2.4 Hz); 7.2–8.2 (5H, aromatic protons).

EXAMPLE 23

A mixture of diastereoisomeric esters G and H prepared as described in ex. 22 (ratio G:H=86:14) (0.64 g; 1.28 mmoles), dimethoxyethane (9 ml) and 12N HCl (9 ml) is kept at 95° C. (temperature of the bath) under stirring for 1 h.

It is cooled to room temperature and then it is worked up as described in ex. 10(b). The so obtained crude acid is eluted through a silica gel column (eluent hexane:diethylether=1:1).

The 2-(5-bromo-6-methoxy-2-naphthyl)-propionic acid is obtained.

M.p.=149°–151° C. and $[\alpha]_{578}^{20}=+33.94°$ (c=0.5%, CHCl$_3$).

A sample is esterified with diazomethane and the obtained methylester is analysed with $^1$H-NMR (200 MHz). Using an optically active shift agent (europium (III) tris[3-(eptafluoropropyl hydroxymethylene)-d-camphorate] in CDCl$_3$ The enantiomers ratio is S(+):R(−)=86:14.

EXAMPLE 24

Preparation of 2-ethyl-2-(6-methoxy-2-naphthyl)-1.3-dioxolane-4(S),5(S)-dicarboxylic acid dimethylester.

1-(6-methoxy-2-naphthyl)-propan-1-one (20 g; 0.093 moles), dimethylester of D(−)tartaric acid (129 g) and trimethyl orthoformate (29 g; 0.27 moles) are gradually heated up to a complete solution. It is then added methanesulphonic acid (0.74 g; 7.7 mmoles) and the solution is refluxed (84° C.) for 1 h; it is cooled to room temperature and the mixture is poured slowly in a 10% solution of Na$_2$CO$_3$ (250 ml) under vigorous stirring.

The mixture is extracted with CH$_2$Cl$_2$ (250 ml) and the organic extracts are washed with water.

The organic phase is dried on Na$_2$SO$_4$ and the solvent is evaporated under reduced pressure.

The crude product (40.3 g) is gradually heated up to 180° C. at 0.1–0.5 mm/Hg, under stirring.

The residue (33.3 g) is crystallized from methanol (100 ml) thus obtaining the desired product (23.7 g; 0.0635 moles; yield 68%) with the following characteristics:

m.p. 72°–73° C.; $[\alpha]_D^{20}=-34.0°$ (c=1%, CHCl$_3$).
I.R. (Nujol): 1770, 1740 cm$^{-1}$ (stretching C=O).
$^1$H-NMR (CDCl$_3$, TMS) (200 MHz).

These data are identical to those of the compound 2-ethyl-2-(6-methoxy-2-naphthyl)-1.3-dioxolane-4(R),5(R)-dicarboxylic acid dimethyl ester, described in ex. 1.

EXAMPLE 25

Preparation of 2-(1-bromoethyl)-2-(5-bromo-6-methoxy-2-naphthyl)-1,3-dioxolane-4(S),5(S)-dicarboxylic acid dimethyl ester.

By processing as described in ex. 19 the 2-ethyl-2-(6-methoxy-2-naphthyl)-1,3-dioxolane-4(S),5(S)-dicarboxylic acid dimethyl ester (9.35 g; 0.025 moles) the desired mixture of diastereoisomers is obtained (identified as 3' and 4') in 93% yield.

The ratio between the diastereoisomers as determined by HPLC is 3':4'=93:7. The diastereoisomer 3', that is the prevailing one is the enantiomer of the diastereoisomer 3 described in ex. 6.

$^1$H-NMR (CDCl$_3$-TMS) (200 MHz).

Diastereoisomer 3' (SSR): the data are identical to those of the diastereoisomer 3 described in ex. 6.

Diastereoisomer 4' (SSS): the data are identical to those of the diastereoisomer 4 described in ex. 6.

HPLC analysis performed as described in ex. 6.
Diastereoisomer 3': retention time 18.41 min.
Diastereoisomer 4': retention time 19.33 min.

EXAMPLE 26

Preparation of 2(S)-hydroxy-3(S)-[2-(5-bromo-6-methoxy-2napthyl)-propanoyl]-butanedioic acid dimethyl ester.

By processing as described in ex. 17, a diastereoisomeric mixture of 2-(1-bromoethyl)-2-(5-bromo-6-methoxy-2-naphthyl)-1,3-dioxolane-4(S),5(S)-dicarboxylic acid dimethyl ester (compounds 3' and 4' of ex. 25 in ratio 3':4'=93:7; 2.66 g; 5.0 mmoles) a mixture of the desired diastereoisomers is obtained (1.98 g; 4.2 mmoles; yield 84.4%) identified as compounds C' and D').

The ratio determined by $^1$H-NMR (200 MHz) is C':D'=85:15.

$^1$H-NMR (CDCl$_3$-TMS) (200 MHz).

Diastereoisomer C' (SSR): the data are identical to those of diastereoisomer C described in ex. 9.

Diastereoisomer D' (SSS): the data are identical to those of diastereoisomer D described in ex. 9.

EXAMPLE 27

Preparation of R(−)-2-(5-bromo-6-methoxy-2-naphthyl)-propionic acid.

A mixture of diastereoisomers C' and D' prepared according to ex. 26 (ratio C':D'=85:15; 1.2 g; 2.56 mmoles), dimethoxyethane (18 ml), 12N HCl (18 ml) is kept at 88° C. under stirring for 1 h.

The reaction mixture is cooled to room temperature and is then worked up as described in ex. 10 (b).

The so obtained crude acid is eluted through a silica gel column (eluent hexane: diethylether 1:1).

The 2-(5-bromo-6-methoxy-2-naphthyl) propionic acid is obtained.

M.p.=146°-148° C.; $[\alpha]_{578}^{20}$=−33.39° (c=0.5%; CHCl$_3$).

This acid is esterified with diazomethane and the obtained methylester analyzed by $^1$H-NMR (200 MHz) using an optically active shift agent (europium (III)-tris[3-(eptafluoropropylhydroxymethylene)-d-camphorate] in CDCl$_3$.

The ratio between the enantiomers is R(−):S(+)=85:15.

The methylester when crystallized from methanol and hydrolized with an acid, leads to the R(−)-2-(5-bromo-6-methoxy-2-naphthyl)-propionic acid in optically pure form.

EXAMPLE 28

Preparation of 2-ethyl-2-(6-methoxy-2-naphthyl)-1,3-dioxolane-4(R),5(R)-dicarboxylic acid dimethyl ester.

1-(6-methoxy-2-naphthyl)-propan-1-one (465 g; 2.17 moles), dimethylester of L(+) tartaric acid (773 g; 4.34 moles) and trimethyl orthoformate (461 g; 4.34 moles) are gradually heated up to complete solution. The solution is added with methanesulphonic acid (15 g; 0.155 moles). The reaction mixture is kept at 100° C. for 4 hours, distilling off the volatile compounds (about 400 g).

It is cooled to 50° C. and poured slowly under stirring into a 10% aqueous solution of NaHCO$_3$ (5 l). It is extracted with CH$_2$Cl$_2$ and the organic extract is washed with water and dried on Na$_2$SO$_4$.

By evaporating the solvent under reduced pressure, a residue containing the desired product as determined by HPLC analysis (743 g; yield 91.6%) is obtained.

An analitycally pure product is obtained by crystallizing from 1.3 l of methanol (672 g; 1.8 moles; yield 82.8%).

EXAMPLE 29

Preparation of the 2-ethyl-2-[4-(2-methylpropyl)-phenyl]-1,3-dioxolane-4(R),5(R)-dicarboxylic acid dimethylester.

A mixture of 1-[4-(2-methylpropyl)-phenyl]-propan-1-one (110 g; 0.58 moles), dimethyl ester of L(+) tartaric acid (206 g; 1.16 moles) and trimethyl orthoformate (122.7 g; 1.16 moles) is gradually heated up to complete solution (50° C. The solution is added with methanesulphonic acid (3.9 g; 0.04 moles).

The reaction mixture is heated to 85° C. and kept at this temperature for 2 h, then cooled to room temperature and worked up as described in ex. 1.

The crude product (210 g) is eluted through a silica gel column (eluent hexane:diethylether=8:2) and the desired product is obtained (175.2 g; 0.501 moles; yield 86.5%) having the following characteristics:

I.R. (Neat): 1730–1760 cm$^{-1}$ (stretching C=0).

$^1$H-NMR (CDCl$_3$-TMS) (200 MHz) delta (ppm): 0.84 (d, 6H, J=6.4 Hz); 0.89 (t, 3H, J=7.5 Hz); 1.8 (t-ept, 1H, J$_{CH-CH_3}$-6.4 Hz, J$_{CH-CH_2}$=7.1 Hz); 1.97 (q, 2H, J=7.5 Hz); 2.41 (d, 2H, J=7.1 Hz); 3.78 (s, 3H); 3.84 (s, 3H); 4.78 (AB, 2H, J=5.7 Hz); 7–7.4 (AA'BB', 4H, aromatic protons).

EXAMPLE 30

Preparation of diastereoisomers of the compound 2-(1-bromoethyl)-2-[4-(2-methylpropyl)-phenyl]-1,3-dioxolane-4(R),5(R)-dicarboxylic acid dimethyl ester.

To a solution in 1,2-dichloroethane (70 ml) of 2-ethyl-2-[4-(2-methylpropyl)-phenyl]-1,3-dioxolane-4(R),5(R)-dicarboxylic acid dimethylester (7.0 g; 20 mmoles obtained according to ex. 29), deoxygenated and added with hydrobromic acid (0.324 g; 4 mmoles), it is added dropwise in 1 h under inert atmosphere at +15° C., a solution of bromine (3.20 g; 20 mmoles) in 1,2-dichloroethane (7.0 ml) previously deoxygenated.

The mixture is kept at 15° C. for an additional hour and then worked up as described in example 6.

The so obtained residue is eluted through a silica gel column (eluent hexane:diethylether 8:2) to give a mixture of the desired diastereoisomers, identified as 11 and 12, in 77% yield.

The ratio between the compounds 11 and 12 as determined by HPLC is 88:12 $^1$H-NMR (CDCl$_3$-TMS) (200 MHz):

Diastereisomer 11 (RRS): delta (ppm): 0.87 (d, 6H, J=6.4 Hz); 1.61 (d, 3H, J=7.1 Hz); 1.84 (t-ept, 1H, J$_{CH-CH_3}$=6.4 Hz, J$_{CH-CH_2}$=7.1 Hz); 2.45 (d, 2H, J=7.1 Hz); 3.53 (s, 3H); 3.84 (s, 3H); 4.38 (q, 1H, J=7.1 Hz) 4.9 (AB, 2H, J=5.9 Hz); 7—7.4 (AA'BB', 4H, aromatic protons).

Diastereoisomer 12 (RRR): delta (ppm): 0.87 (d, 6H, J=6.4 Hz); 1.58 (d, 3H, J=7.1 Hz); 1.87 (t-ept, 1H, J$_{CH-CH_3}$=6.4 Hz, J$_{CH-CH_2}$=7.1 Hz); 2.53 (d, 2H, J=7.1 Hz); 3.6 (s, 3H); 3.83 (s, 3H); 4.41 (q, 1H, J=7.1 Hz); 4.85 (AB, 2H, J=6.5 Hz); 7–7.4 (AA'BB', 4H, aromatic protons).

The HPLC analysis has been performed under the following conditions: Hewlett Packard instrument mod. 1090 with a variable wavelength UV detector (mod. 1040 DAD).

Analytical conditions:
  column BROWNLEE LABS RPS (5μ) spheri, 250 mm×4.6 mm (internal diameter)
  solvent A: bidistilled water
  solvent B: acetonitrile:methanol=40:60
  flow 2 ml/min.
  percentage solvent B: 54%
  column temperature: 50° C.
  wavelength (λ): 222 nanometers
  injection 4 μl of a solution containing 0.5 mg/ml of product in acetonitrile:methanol 40:60
  retention times: diast. 11=22.61 min., diast. 12=23.63 min.

EXAMPLE 31

Preparation of 2(R)-hydroxy-3(R)-(2-[4-(2-methylpropyl)-phenyl]-propanoyl-butanedioic acid dimethyl ester.

Operating under analogous conditions to those described in Example 17, after work up of the reaction mixture, starting from a mixture of diastereoisomers 11 and 12 (3.0 g; 7.0 mmoles) (ratio determined by HPLC, 11:12=88:12), with a reaction time of 6 hours at +28° C. the mixture of diastereoisomeric esters indicated herein as I and j is obtained.

$^1$H-NMR (CDCl$_3$-TMS) (200 MHz).

Diastereoisomer I (RRS): delta (ppm): 0.87 (d, 6H, J=6.4 Hz); 1.485 (d, 3H, J=7.1 Hz); 1.8 (t-hept, 1H, J$_{CH-CH33}$=6.4 Hz, J$_{CH-CH2}$=7.1 Hz); 2.42 (d, 2H, J=7.1 Hz); 4.67 (dd, 1H, J$_{CH-CH}$=2.3 Hz, J$_{CH-OH}$=7.05 Hz); 5.36 (d, 1H, J=2.3 Hz); 7.02–7.16 (AA'BB', 4H, aromatic protons).

Diastereoisomer J (RRR): delta (ppm): 0.87 (d, 6H, J=6.4 Hz); 1.525 (d, 3H, J=7.1 Hz); 1.825 (t-hept, 1H, J$_{CH-CH3}$=6.4 Hz, J$_{CH-CH2}$=7.1 Hz); 2.43 (d, 2H, J=7.1 Hz); 3.15 (d, 1H, J=7.05 Hz); 3.62 (s, 3H); 3.69 (s, 3H); 3.82 (q, 1H, J=7.1 Hz); 4.73 (dd, 1H, J$_{CH-CH}$=2.3 Hz, J$_{CH-CH}$=7.05 Hz); 5.43 (d, 1H, J=2.3 Hz); 7.04–7.2 (AA'BB', 4H, aromatic protons).

EXAMPLE 32

Preparation of 2-[4-(2-methylpropyl)-phenyl]-propionic acid (Ibuprofen).

Operating in a analogous manner to that described in Example 10(b), crude 2-[4-(2-methylpropyl)-phenyl]-propionic acid is obtained from a mixture of diastereoisomeric esters I and J, prepared as described in Example 31 (1.37 g; 3.74 mmoles). After chromatography a silica gel, the pure acid is obtained (0.7 g).

$[\alpha]_D^{20}$= +19° (C=1%, 95% ethanol).

EXAMPLE 33

Preparation of 2-(1-bromoethyl)-2-[4-(2-methylpropyl)-phenyl]-1,3-dioxolane-4(R),5(R)-dicarboxylic acid.

A solution of diastereoisomers 11 and 12 (see Example 30)(10.0 g; 0.0233 moles) in methylene chloride (20 ml) is added dropwise to a solution of sodium hydroxide (1.87 g; 0.0466 moles) in water 25 ml) and methanol (100 ml), kept under stirring at 20° C. The reaction mixture is kept under stirring at this temperature for 1 hour. The solvent is evaporated under reduced pressure. The residue is taken up in water (100 ml) and acidified to pH 1, with concentrated HCl.

It is extracted with diethylether (3×50 ml). The organic phase is extracted with a 10% sodium bicarbonate solution (3×50 ml).

The alkaline solution is acidified to pH 1, with concentrated HCl and extracted with diethylether (3×50 ml). The combined organic phases are dried over sodium sulphate, and the solvent is evaporated under reduced pressure to give the crude product (8.3 g; acidimetric assay 92%; yield 81%).

HPLC analysis of a sample esterified with diazomethane shows that the ratio of the two diastereoisomers 13 and 14 is 87:13.

$^1$H-NMR (CDCl$_3$-TMS) delta (ppm).

Diastereoisomer 13 (RRS): delta (ppm): 0.87 (d, 6H, J=6.4 Hz); 1.59 (d, 3H, J=7.1 Hz); 1.95 (t-ept, 1H, J$_{CH-CH3}$=6.4 Hz, J$_{CH-CH2}$=7 Hz); 2.55 (d, 2H, J=7 Hz); 4.42 (q, 4.42 (q, 1H, J=7.1 Hz); 4.88 (AB, 2H, J=6.4 Hz); 7–7.4 (AA'BB', 4H, aromatic protons); 8.2 (s, 2H).

Diastereoisomer 14 (RRR): delta (ppm): 0.87 (d, 6H, J=6.4 Hz); 1.58 (d, 3H, J=7.1 Hz); 1.95 (t-ept, 1H, J$_{CH-CH3}$=6.4 Hz, J$_{CH-CH2}$=7 Hz); 2.55 (d, 2H, J=7 Hz); 4.42 (q, 1H, J=7 Hz); 4.8 (AB, 2H, J=6.4 Hz); 7–7.44 (AA'BB', 4H, aromatic protons); 8.2 (s, 2H).

EXAMPLE 34

Preparation of (+)-2(R)-hydroxy-3(R)-[2(S)(6-methoxy-2-naphthyl)propanoyl]-butanedioic acid dimethyl ester.

A solution of triethylamine (4.45 g; 0.044 moles) in methylene chloride (10 ml) is added dropwise in a period of 5 minutes to a mixture of 2(R),3(R)-dihydroxybutanedioic acid dimethyl ester (L(+)tartaric acid dimethyl ester)(44.5 g; 0.25 moles) and methylene chloride (90 ml), cooled to −10° C. and kept under stirring, followed by the dropwise addition in a period of 20 minutes of a solution, in methylene chloride (25 ml) of S(+)2-(6-methoxy-2-naphthyl)-propionyl chloride (5.0 g; 0.020 moles) prepared as described in Japanese patent application 57/145841 (C.A. 98, 72492h).

The reaction mixture is then poured into a 10% sodium bicarbonate solution (200 ml), extracted with methylene chloride (100 ml), and the organic phase washed with dilute hydrochloric acid and dried over sodium sulphate. The residue (5.5 g) is obtained by evaporating the solvent under reduced pressure, and is crystallised from a mixture of heptane and diethylether (1:1, 165 ml).

The desired product (diastereoisomer A, see Example 3) (2.75 g) is obtained, having the following characteristics:

I.R. (C=5% in CHCl$_3$) 1750 cm$^{-1}$.
$[\alpha]_D^{20}$= +73.7° (C=1%, CHCl$_3$).
M.P.=77°–79° C.

$^1$H-NMR (CDCl$_3$-TMS) (200 MHz): delta (ppm): 1.58 (d, 3H, J=7.4 Hz); 3.07 (s, 3H); 3.31 (d, 1H, J=7.4 Hz); 3.79 (s, 3H); 3.87 (s, 3H); 3.96 (q, 1H, J=7.4 Hz); 4.66 (dd, 1H, J$_{CH-CH}$=2.3 Hz, J$_{CH-OH}$=7.4 Hz); 5.37 (d, 1H, J=2.3 Hz); 7–7.8 (6H, aromatic system).

A solution of bromine (0.410 g; 2.56 mmoles) in 1,2-dichloroethane (3 ml) is added in 15 minutes to a solution of the ester thus obtained in 1,2-dichloroethane (10 ml), cooled to 0° C.

The reaction mixture is kept at 0° C. for 1 hour, and is then poured into a 10% sodium bicarbonate solution (10 ml) and extracted with methylene chloride (10 ml).

The combined organic phases are washed with water (20 ml×2), dried over sodium sulphate, and the solvent evaporated under reduced pressure.

The residue (1.14 g) is crystallized from methanol. (+)-2(R)-hydroxy-3(R)-[2-(S)-(5-bromo-6-methoxy-2-naphthyl)-propanoyl)]-butanedioic acid dimethyl ester is obtained (0.889 g; 1.9 mmoles; yield 74%); M.P. 124°–126° C.; $[\alpha]_D^{20}$= +61.4° (C=1%; CHCl$_3$).

The chemical-physical data (M.P., $[\alpha]_D^{20}$ and $^1$H-NMR-200 MHz) are equal to those of the diastereoisomer ester C described in Example 9. When treated with palladium-on-carbon and hydrogen at atmospheric pressure and room temperature in the presence of triethylamine, the product produces the diastereoisomer A.

EXAMPLE 35

Preparation of the mixture of diastereoisomers 7 and 8 of 2-(1-bromoethyl)-2-(5-bromo-6-methoxy-2-naphthyl)-1,3-dioxolane-4(R),5(R)-dicarboxylic acid.

A solution of bromine (171 g; 1.68 moles) in carbon tetrachloride (360 ml) is added dropwise in 1 hour to a solution of 2-ethyl-2-(6-methoxy-2-naphthyl)-1,3-dioxolane-4(R),5(R)-dicarboxylic acid dimethyl ester (200 g; 0.534 moles) in carbon tetrachloride (2000 ml) kept under an inert atmosphere at 0° C.

The reaction mixture is kept at 0° C. for 2 hours, and worked as described in Example 6.

The crude product thus obtained (351 g) is dissolved in methanol (2000 ml), and a solution of sodium hydroxide (38.4 g; 0.96 moles) in water (384 ml) is added dropwise to the resultant solution at ambient temperature in 1 hour. The reaction mixture is kept at ambient temperature under stirring for 20 hours. The methanol is evaporated under vacuum, maintaining the initial volume of the solution by adding water.

The pH of the aqueous solution obtained is adjusted to 7 with dilute hydrochloric acid. The solution is then extracted with methylene chloride and the aqueous solution is acidified with concentrated HCl to pH 1.

It is extracted with diethylether (3×250 ml) and the combined organic phases are washed with water and dried over sodium sulphate. The solvent is evaporated under vacuum to give a residue that is crystallised from methylene chloride.

A mixture of the two diastereoisomers 7 and 8 of 2-(1-bromoethyl)-2-(5-bromo-6-methoxy-2-naphthyl)-1,3-dioxolane-4(R),5(R)-dicarboxylic acid is obtained (205 g; 0.407 moles; yield 76%) in the ratio of 7:8=94.6.

EXAMPLE 36

A mixture of the two diastereoisomers 3 and 4 of 2-(1-bromoethyl)-2-(5-bromo-6-methoxy-2-naphthyl)-1,3-dioxolane-4(R),5(R)-dicarboxylic acid dimethyl ester in the ratio 3:4=9:1 (1 g; 1.87 mmoles), zinc bromide (0.84 g; 3.75 mmoles) and 1,2-dichloroethane (12 ml) is heated at reflux (83° C.), under stirring and under nitrogen, for 66 hours.

The reaction mixture is cooled to ambient temperature, and water (5 ml) is added. The phase are separated and the organic phase is dried over sodium sulphate.

The solvent is evaporated under vacuum to give a residue (0.9 g) to which dioxane (10 ml) and concentrated HCl (5 ml) are added. The mixture is heated to 70° C. under, stirring, for 2 hours, is then diluted with water (10 ml) and extracted with diethylether (3×20 ml).

The combined organic extracts are washed with water and dried over sodium sulphate. Evaporation of the solvent under vacuum gives a residue which by chromatography on silica gel (eluent hexane:ethyl ether=7:3) gives 2-(5-bromo-6-methoxy-2-naphthyl)-propionic acid (0.28 g; 0.9 mmoles; yield 48%).

M.P. 166°-167° C.

$[\alpha]_D^{20} = +15.44°$ (C=0.5, CHCl$_3$).

The ratio of the enantiomeric acids S(+)/R(−) is 65:35.

EXAMPLE 37

Preparation of 2-(S)-(5-bromo-6-methoxy-2-naphthyl)-propionic acid methyl ester from 2-(1-(S)-bromoethyl)-2-(5-bromo-6-methoxy-2-naphthyl)-1,3-dioxolane-4(R),5(R)-dicarboxylic acid dimethyl ester.

A mixture of pure 2-(1-(S)-bromoethyl)-2-(5-bromo-6-methoxy-6-methoxy-2-naphthyl)-1,3-dioxolane-4(R),5(R)-dicarboxylic acid dimethyl ester (1.03 g, 1.93 mmol), silver trifluoromethanesulfonate (0.6 g, 2.31 mmol) and methanol (5 ml) is heated at reflux for 7 hours. The reaction mixture is cooled at room temperature, filtered, poured into water, and extracted with dichloromethane. The combined organic extracts are washed with water, dried (Na$_2$SO$_4$), and filtered.

Evaporation of the solvent under reduced pressure gives the optically pure 2-(S)-(5-bromo-6-methoxy-2-naphthyl)-propionic acid methyl ester.

M.P. 94°-95° C.

$[\alpha]_D^{20} = +52°$(c=0.5, CHCl$_3$).

The product is found to be optically pure by $^1$H-NMR (200 MHz) analysys, carried out in CDCl$_3$ using an optically active shifting agent (Europium (III) Tris-[3-(eptafluoropropylhydroxymethylene)-d-camphorate].

EXAMPLE 38

Bromination of 2-ethyl-2-(6-methoxy-2-naphthyl)-1,3-dioxolane-4(R),5(R)-dicarboxylic acid.

Bromine (0.32 g; 2 mmol) is added dropwise, in 5 minutes at 15° C. and under argon, to a suspension of 2-ethyl-2-(6-methoxy-2-naphthyl)-1,3-dioxolane-4(R),5(R)-dicarboxylic acid (0.346 g, 1 mmol). The reaction mixture is heated at 40° C. and kept at 40° C. for 12 hours; then it is poured into a 10% aqueous solution of sodium bicarbonate and extracted with diethylether. The aqueous phase is acidified to pH=1 with conc. HCl and extracted with diethylether. The combined organic extracts are washed with water, dried (Na$_2$SO$_4$), and filtered. Evaporation of the solvent under reduced pressure gives a reaction crude which, after purification leads to a diastereoisomeric mixture of 2-(1-bromoethyl)-2-(5-bromo-6-methoxy-2-naphthyl)-1,8-dioxolane-4(R),5(R)-dicarboxylic acid in ratio 7:8=81:19 (determined by $^1$H-NMR).

$^1$H-NMR (90 MHz, Acetone-d$_6$-TMS) δ (ppm).

Diastereoisomer 7 (RRS): 1.70 (3H, d, J=6.8 Hz); 4.03 (3H, s); 4.66 (1H, q, J=6.8 Hz); 4.95 (2H, ABq, Δν=15.31, J=6.9 Hz); 7.45-8.18 (5H, m).

Diastereoisomer 8 (RRR): 1.70 (3H, d, J=6.8 Hz); 4.03 (3H, s); 4.66 (1H, q, J=6.8 Hz); 4.95 (2H, ABq, Δν=14.46, J=6.6 Hz); 7.45-8.18 (5H, m).

The diastereoisomeric ratio is confirmed analyzing by $^1$H-NMR and HPLC the product obtained by esterification with diazomethane.

EXAMPLE 39

Preparation of the diastereoisomeric mixture of 2-(1-iodoethyl)-2-(6-methoxy-2-naphthyl)-1,3-dioxolane-4(R),5(R)-dicarboxylic acid dimethyl ester.

A solution of 2 -ethyl-2-(6-methoxy-2-naphthyl)-1,3-dioxolane-4(R),5(R)-dicarboxylic acid dimethyl ester (0.935 g, 2.5 mmol) and of iodine monochloride (0.81 g, 5 mmol) in dichloromethane (5 ml) is kept under nitrogen and at 15° C. for 24 hours. The reaction mixture is poured into a 10% aqueous solution of sodium bicarbonate, and extracted with additional dichloromethane. The combined organic extracts are washed with a 5% aqueous solution of sodium thiosulphate, with water, dried (Na$_2$SO$_4$), filtered, and concentrated in vacuo. Purification of the residue by column chromatography (silical gel, eluent hexane:diethyl ether=7:3) gives the diastereoisomeric mixture of 2-(1-iodoethyl)-1-iodoethyl)-2-methoxy-2-naphthyl)-1,3-dioxolane-4(R),5(R)-dicarboxylic acid dimethyl ester 15 and 16 in ratio 15:16=60:40 (determined by $^1$H-NMR).

$^1$H-NMR (200 MHz, CDCl$_3$-TMS) δ (ppm).

Diastereoisomer 15 (RRS) 1.80 (3H, d, J=7 Hz); 3.44 (3H, s); 3.84 (3H, s); 3.90 (3H, s); 4.58 (1H, q, J=7 Hz); 4.95 (2H, ABq, Δν=20.70, J=6 Hz); 7.8–8.0 (6H, m).

Diastereoisomer 16 (RRR): 1.80 (3H, d, J=7 Hz); 3.58 (3H, s); 3.84 (3H, s); 3.90 (3H, s); 4.58 (1H, q, J=7 Hz); 4.87 (2H, ABq, Δν=46.04, J=6.8 Hz); 7.8–8.0 (6H, m).

EXAMPLE 40

Preparation of 2-(6-methoxy-2-naphthyl)-propionic acid from a diastereoisomeric mixture of 2-(1-iodoethyl)-2-(6-methoxy-2-naphtyl)-1,3-dioxolane-4(R),5(R)-dicarboxylic acid dimethyl ester.

Silver trifluoromethanesulfonate (1.2 g, 4.8 mmol) is added, under argon and stirring, at 15° C. to solution of a diastereoisomeric mixture of 2-(1-iodoethyl)-2-(6-methoxy-2-naphthyl)-1,3-dioxoalane-4(R),5(R)-dicarboxylic acid dimethyl ester in ratio 60:40 (1.6 g, 3.2 mmol) in 1,2-dichloroethane (20 ml). The reaction mixture is kept in the dark at 15° C. for 3 hours; then it is filtered, poured into water. The organic layer is separated, washed with water, dried (Na$_2$SO$_4$), filtered and concentrated in vacuo.

The residue is dissolved into dioxane (5 ml) and conc. HCl (5 ml) is added. The mixture is heated at 70° C. for 2 hours cooled at room temperature, poured into water, and extracted with diethyl ether.

The combined organic extracts are washed with water and back-extracted with a 2% aqueous solution of sodium bicarbonate. The aqueous phase is acidified with conc. HCl and extracted with diethyl ether. The combined organic extracts are washed with water, dried (Na$_2$SO$_4$), filtered. Evaporation of the solvent under reduced pressure gives the 2-(6-methoxy-2-naphthyl)-propionic acid.

M.p.=154°–156° C.

$[\alpha]_D^{20} = +6.02$ (c=1, CHCl$_3$).

HPLC analysis, carried out as described in J. Pharm. Sci. 68, 112 (1979) and H-NMR (200 MHz) analysis carried out on the methyl ester in CDCl$_3$ using an optically active shifting agent (Europium (III) Tris-[3(eptafluoropropylhydroxymethylen)-d-camphorate]) shows an enantiomeric ratio S(+):R(−)=55:45.

EXAMPLE 41

Preparation of 2-ethyl-2-(6-hydroxy-2-naphtyl)-1,3+-dioxolane-4(R),5(R)-dicarboxylic acid dimethyl ester.

A mixture of 1-(6-hydroxy-2-naphtyl)-propan-1-one (25 g, 0.125 mol), 2(R),3(R)-dihydroxybutanedioic acid dimetyl ester (178 g, 1 mol), trimethyl orthoformate (54 g. 0.51 mol), and of methanesulphonic acid (0.84 g, 0.088 mol) is heated, under argon and under stirring, at 70° C. for 4 hours.

The reaction mixture is cooled at room temperature, poured into a 10% aqueous solution of sodium carbonate (400 ml), and extracted with diethylether (4×50 ml). The combined organic extracts are washed with water (3×150 ml), dried (Na$_2$SO$_4$), filtered, and concentrated in vacuo.

Purification of the crude by column chromatography (silica gel, eluent hexane:diethylether=1:1) gives the pure 2-ethyl-2-(6-hydroxy-2-naphtyl)-1,3-dioxolane-4(R),5(R)-dicarboxylic acid dimethylester (17 g) as an oil.

$^1$H-NMR (90 MHz, CDCl$_3$-TMS) δ (ppm): 1.93 (3H, t, J=6.5 Hz); 2.10 (2H, q, J=6.5 Hz); 3.43 (3H, s); 3.80 (3H, s); 4.83 (2H, ABq, Δν=6.7, J=6 Hz); 6.00 (1H, s, OH); 7.07–7.85 (6H, m).

EXAMPLE 42

Preparation of the diastereoisomeric mixture of 2-(1-bromoethyl)-2-(5-bromo-6-hydroxy-2-naphthyl)-1,3-dioxolane-4(R),5(R)-dicarboxylic acid dimethyl ester.

A solution of bromine (5.12 g, 32 mmol) in carbon tetrachloride (5 ml) is added dropwise in 10 minutes, under argon and at 15° C., to a solution of 2-ethyl-2-(6-hydroxy-2-naphthyl)-1,3-dioxolane-4(R),5(R)-dicarboxylic acid dimethyl ester (6 g, 16 mmol) in carbon tetrachloride (60 ml). The reaction mixture is kept at 15° C. for 2 hours and poured into a 5% aqueous solution of sodium thiosulfate (200 ml).

The organic layer is separated, washed with water, dried (Na$_2$SO$_4$), filtered, and concentrated in vacuo.

Purification of the reaction crude by column chromatography (silica gel, hexane:diethyl ether=1:1) gives a diastereoisomeric mixture of 2-(1-bromoethyl)-2-(5-bromo-6-hydroxy-2-naphthyl)-1,3-dioxolane-4(R),5(R)-dicarboxylic acid dimethyl ester (8 g, 15 mmol; yield 93%) as a solid.

Ratio diastereoisomers 17:18=90:10 (determined by $^1$H-NMR and HPLC).

m.p. 116°–117° C.

$^1$H-NMR (200 MHz, CDCl$_3$TMS) δ (ppm).

Diastereoisomer 17 (RRS): 1.66 (3H, d, J=7 Hz); 3.52 (3H, s); 3.88 (3H, s); 4.48 (1H, q, J=7 Hz): 4.96 (2H, ABq, Δν=27.80, J=6.1 Hz); 7.2–8.0 (5H, m).

Diastereoisomer 18 (RRR): 1.62 (3H, d, J=7 Hz); 3.56 (3H, s); 3.87 (3H, s); 4.48 (1H, q, J=7 Hz); 4.90 (2H, ABq, Δν=35.44, J=6.3 Hz); 7.2–8.0 (5H, m).

The diastereoisomeric ratio 17(RRS):18(RRR)=90:10 is confirmed by converting the product in the diastereoisomeric mixture of 2-(1-bromoethyl)-2-(5-bromo-6-methoxy-2-naphthyl)-1,3-dioxolane-4(R),5(R)-dicarboxylic acid dimethyl eser 3 and 4 following the present procedure: a mixture of the product (0.52 g, 1 mmol), potassium carbonate (1.38 g, 10 mmol), methyl iodide (0.426 g, 3 mmol), and of acetone (10 ml) is kept under stirring at room temperature for 4 hours.

The reaction mixutre si filtered and concentrated in vacuo. The residue, so obtained, is a diastereoisomeric mixture of 2-(1-bromoethyl)-2-(5-bromo-6-methoxy-2-naphthyl)-1,3-dioxolane-4(R),5(R)-dicarboxylic acid dimethyl ester in ratio 3(RRS):4(RRR)=90:10 (determined by $^1$H-NMR and HPLC).

EXAMPLE 43

Preparation of 2-(5-bromo-6-hydroxy-2-naphthyl)-propionic acid.

A mixture of the diastereoisomers 17 and 18 in the ratio 90:10 (see Example 42) (0.57 g; 11 mmoles), sodium hydroxide (0.132 g; 33 mmoles) and water (20 ml) is heated to 60° C. for 2 hours. The reaction mixture is cooled to room temperature, acidified to pH 1 with concentrated HCl and extracted with diethylether.

The combined organic phases are washed with water, dried over sodium sulphate and concentrated under vacuum. The residue thus obtained is purified by chromatography on silica gel, to give pure 2-(5-bromo-6-hydroxy-2-naphthyl)-propionic acid.

On the basis of $^1$H-NMR analysis as described in Example 4, the ratio of the S to R enantiomer is 90:10.

EXAMPLE 44

Preparation of 2-(1-bromoethyl)-2-(5-bromo-6-hydroxy-2-naphthyl)-1,3-dioxolane-4(R),5(R)-dicarboxylic acid.

A mixture of the diastereoisomers 17 and 18 in the ratio 90:10 (see Example 42) (5.6 g; 0.0108 moles), water (52 ml), methanol (30 ml) and an aqueous 10% (w/v) sodium hydroxyde solution (11.5 ml) is kept under stirring at room temperature for 6 hours.

The reaction mixture is then acidified with concentrated HCl to pH 1 and extracted with diethylether. The combined organic extracts are washed with water and dried over sodium sulphate.

Evaporation of the solvent under vacuum gives the diastereoisomers 19 and 20 (4.8 g; 0.0098 moles; yield 90%) in the ratio 19:20=92.8

$^1$H-NMR (90 MHz, CDCl$_3$-TMS) δ (ppm).

Diastereoisomer 19 (RRS): 1.66 (d, 3H, J=7 Hz); 4.63 (q, 1H, J=7 Hz); 4.93 (2H, ABq, Δν=16.42, J=6.5 Hz); 7.23–8.15 (m, 5H); 8.27 (1H, broad).

EXAMPLE 45

Preparation of 2-(5-bromo-6-hydroxy-2-naphthyl)-propionic acid

A mixture of the diastereoisomers 2-(1-bromoethyl)-2-(5-bromo-6-hydroxy-2-naphthyl)-1,3-dioxolane-4(R),5(R)-dicarboxylic acid 19 and 20 (1.76 g; 3.6 mmoles) in the ratio 19:20=92.8 (see Example 44), sodium bicarbomate (2.4 g; 28 mmoles) and water (50 ml) is heated under reflux, under stirring, for 4 hours. The reaction mixture, cooled to ambient temperature, is acidified to pH 1 with 6N HCl and extracted with deithylether. The combined organic phases are washed with water and dried over sodium sulphate. Evaporating the solvent under vacuum gives a crude product to which dimethoxyethane (17 ml) and 12N HCl (17 ml) are added. The reaction mixture is heated under reflux, under stirring for 2 hours, cooled and extracted with diethylether. The combined organic phases are washed with water and dried over sodium sulphate. Evaporation of the solvent under vacuum gives a residue which is chromatographed over silica gel (eluent diethylether-hexane 7:3). In this manner the pure acid is obtained $[\alpha]_D^{20}$= +42.3 (C=1 in acetone). A samples is esterified with diazomethane. The methyl ester is analysed by $^1$H-NMR (200 MHz) using an optically active shift agent. The ratio of the enantiomeric acids (+)S/(−)R is 98.2.

EXAMPLE 46

A solution of silver tetrafluoroborate (0.6 g; 3.08 mmoles) in 1,2-dichloroethane (4 ml) is added dropwise to a mixture of 2-(1-bromoethyl)-2-(5-bromo-6-methoxy-2-naphthyl)-1,3-dioxolane-4(R),5(R)-dicarboxylic acid dimethyl ester (diastereoisomer 3:diastereoisomer 4=94.6, ratio determined by HPLC) (1.33 g; 2.5 mmoles) and 1,2-dichloroethane (10 ml) kept under stirring at +15° C.

After 73 hours the reaction mixture is poured into water (20 ml) and filtered through celite, the filtrate being washed with methylene chloride (10 ml).

The organic phase is washed with water (2×20 ml) and dried over sodium sulphate.

Evaporation of the solvent under reduced pressure gives a residue (0.95 g) in which the diastereoisomers C and D of the ester are present in the ratio C:D=79.21, determined by $^1$H-NMR analysis at 60 MHz.

In an analogous test carried out in parallel, in which water (0.1 g; 6 mmoles) was added to the reaction mixture before adding the sodium tetrafluoroborate, the ratio of the diastereoisomers, after 73 hours, is C:D=94.6.

EXAMPLE 47

Preparation of 1-(4-chlorophenyl)-3-methyl-butan-1one 3-methyl-butyrryl chloride (128.6 g; 1.07 moles) is added in 15 minutes to a suspension of aluminum chloride (153.8 g; 1.15 moles) in methylene chloride (200 ml) cooled to −5° C. and kept under stirring in an inert atmosphere.

At the end of the addition, the mixture is heated to +20° C. and chlorobenzene (100 g; 0.89 moles) is added in 15 minutes. The reaction mixture is heated to +45° C. for 7 hours, then cooled to ambiente temperature and poured under stirring into concentrated HCl (200 ml) and ice (1500 g).

The aqueous phase is extracted with methylene chloride (3×300 ml). The organic extracts are washed with a 1% sodium hydroxide solution (3×700 ml) and with water (3×700 ml).

After drying over sodium sulphate, the organic solvent is evaporated under reduced pressure to give a residue (161 g) which, after crystallization from n-hexane (100 ml) provides 1-(4-chlorophenyl)-3-methyl-butan-1-one (121.5 g; 0.62 moles; yield 69.4%).

M.P.=39–40°.

I.R. (Nujol)=1680–1700 cm$^{-1}$ (stretching c=0).

$^1$H-NMR (CDCl$_3$-TMS) (90 MHz): δ (ppm): 0.97 (d, 6H, J=6,7 Hz); 2.27 (m, 1H, $J_{CH-CH_3}$=6.7 Hz); 2.77 (part AB of an ABX system, 2H); 7.3–7.9 (AA'BB', 4H aromatic protons).

EXAMPLE 48

Preparation of 2-(4-chlorophenyl)-2-(2-methylpropyl)-1,3-dioxolane-4(R),5(R)-dicarboxylic acid dimethyl ester.

A mixture of 1-(4-chlorophenyl)-3-methyl-butan-1-one (40.0 g; 0.204 moles), 2(R),3(R)-dihydroxybutanedioic acid dimethyl ester (72.4 g; 0.407 moles) and trimethyl orthoformate (43.1 g; 0.406 moles) is heated gradually untill a complete solution (60° C.). Methanesulphonic acid (1.4 g; 0.015 moles) is added to the solution, which is then heated to 75° C.

After a reaction time of 3 hours, the mixture is cooled to ambient temperature and poured into a 10% sodium bicarbonate solution (250 ml) under vigorous stirring. The aqueous phase is extracted with methylene chloride (2×250 ml) and the organic extracts washed with water (2×400 ml). After drying the organic phase over sodium sulphase, the solvent is evaporated under reduced pressure.

The residue obtained (68.7 g) is chromatographed over silica gel (eluent hexane:diethylether=8:2).

2-(4-chlorophenyl)-2-(2-methylpropyl)-1,3-dioxolane-4(R),5(R)-dicarboxylic acid dimethyl ester (41 g; 0.115 moles; yield 56.4%) is obtained.

M.P.=40° C.

$[\alpha]_D^{20}$= +21.6° (c=1%; CHCl$_3$).

I.R. (Nujol)=1770–1740 cm$^{-1}$ (stretching c=0).

$^1$H-NMR (200 MHz) (CDCl$_3$-TMS): δ (ppm): 0.87 (d, 6H, J=6.9 Hz); 1.67 (m, 1H, $J_{CH-CH_3}$=6.9 Hz); 1.86 (part AB of an ABX system, 2H); 3.55 (s, 3H); 3.82 (s, 3H); 4.74 (ABq, 2H, J=6.0 Hz); 7.2–7.4 (AA'BB', 4H aromatic protons).

EXAMPLE 49

Preparation of 2-(1-bromo-2-methylpropyl)-2-(4-chlorophenyl)-1,3-dioxolane-4(R),5(R)-dicarboxylic acid dimethyl ester.

A solution of bromine (8.06 g; 0.05 moles) in 1,2-dichloroethane (18 ml) is added in 1 hour and 15 minutes to a solution of 2-(4-chlorophenyl)-2-(2-methylpropyl)-1,3-dioxolane-4(R),5(R)-dicarboxylic acid dimethyl ester (18.0 g; 0.05 moles) in 1,2-dichloroethane (180 ml), to which methanesulphonic acid (3.6 g; 0.038 moles) had been previously added, the reaction mixture being kept under stirring in an inert atmosphere at +15° C. After 1 hours at 15° C., the mixture is poured into a 10% sodium carbonate solution (400 ml) under vigorous stirring and extracted with methylene chloride (2×250 ml).

The organic phase is washed with water (2×400 ml) and dried over sodium sulphate.

After evaporating the solvent under reduced pressure, a residue (20.5 g) is obtained which contains the two diastereoisomers of the 2-(1-bromo-2-methylpropyl)-2-(4-chlorophenyl)-1,3-dioxolane-4(R),5(R)-dicarboxylic acid dimethyl ester, here indicated as 21 and 22, in the ratio 21:22=97:3 (ratio determined by $^1$H-NMR (300 MHz) analysis and confirmed by HPLC analysis).

By crystallization from n-hexane (60 ml), the diastereoisomer 21 is obtained (13.6 g; 0.031 moles; yield 62.5%), and is found to be pure on $^1$H-NMR analysis (300 MHz).

$^1$H-NMR (300 MHz) (CDCl$_3$-TMS).

Diastereoisomer 21 (RRS): 0.93 (d, 3H, J=6.9 Hz); 0.98 (d, 3H, J=6.6 Hz); 1.70 (m, 1H, J$_{CH-CH}$=1.8 Hz, J$_{CH-CH3}$=6.6 Hz, J$_{CH-CH3}$=6.9 Hz); 3.59 (s, 3H); 3.85 (s, 3H); 4.28 (d, 1H, J=1.8 Hz); 4.87 (ABq, 2H, J=6.2 Hz); 7.3-7.5 (AA'BB', 4H aromatic protons).

The HPLC analysis was performed under the following conditions:

Hewlet Packard instrument mod. 1090 with U.V. variable wavelength U.V. detector (mod. 1040 DAD).

Analytical conditions:

Brownlee column LABS RP 8 (5μ) balls; 250 ml×4.6 mm (inner diameter)

Solvent A: bidistilled water
Solvent B: methanol
Flow: 1.7 ml/min
Percentage solvent B: 63%
Column temperature: 40° C.
Wavelength (λ): 230 nanometer
Injection 5μ of a solution containing 0.5 mg/ml of product in methanol
Retention times:
Diastereoisomer 21=11.71 minutes
Diastereoisomer 22=12.85 minutes

EXAMPLE 50

Preparation of 2(R)-hydroxy-3(R)-[2(S)-(4-chlorophenyl)-3-methylbutanoyl]-butanedioic acid dimethyl ester A solution of silver tetrafluoroborate (1.6 g, 8.2 mmol) in 1,2-dichloroethane (15 ml) was added in 20 minutes to a mixture of 2-(1-bromo-2-methylpropyl)-2-(4-chlorophenyl)-1,3-dioxolane-4(R),5(R)-dicarboxylic acid dimethyl ester (diastereoisomer 21) (3 g, 6.9 mmol), water (0.2 g) and of 1,2-dichloroethane (18 ml) at 20° C. The reaction mixture was heated at 50° C. for 7 hours, cooled at 20° C. and poured in water (50 ml). The mixture was filtered on celite and the precipitate washed with dichloromethane (30 ml). The organic phase was separated, washed with water, dried over sodium sulfate, and concentrated in vacuo. Purification of the reaction crude (2.3 g) by column chromatography (silica gel; eluent hexane:diethylether32 1:1) gave the pure diastereoisomer 2(R)-hydroxy-3(R)-[2-(S)-(4-chlorophenyl)-3-methylbutanoyl]-butanedioic acid dimethyl ester K (1.95 g, 5.2 mmol; yield 75.9%).

$^1$H-NMR (300 MHz, CDCl$_3$-TMS) delta (ppm): 0.68 (d, 3H, J$_{CH-CH3}$=6.9 Hz); 1.06 (d, 3H, J=6.2 Hz); 2.33 (m, 1H, J$_{CH-CH}$=10.6 Hz, J$_{CH-CH3}$=6.9 Hz, J$_{CH-CH3}$=6.2 Hz); 3.22 (d, 1H, J$_{CH-CH3}$=6.95 Hz); 3.24 (d, 1H, J=10.6 Hz); 3.30 (s, 3H); 3.77 (s, 3H); 4.63 (dd, 1H, J$_{CH-CH}$=2.6 Hz, J$_{CH-CH}$=2.6 Hz); 5.36 (d, 1H, J$_{CH-CH}$=2.6 Hz); 7.21-7.28 (AA'BB', 4H, aromatic protons).

EXAMPLE 51

Preparation of 2(R)-hydroxy-3(R)-[2(S)-(4-chlorophenyl)-3-methylbutanoyl]-butandioic acid.

A mixture of 2(R)-hydroxy-3(R)-[2(S)-(4-chlorophenyl)-3-methylbutanoyl]-butanedioic acid dimethyl ester (diastereoisomer K) (1 g, 2.6 mmol), 1,2-dimethoxyethane (18.3 ml) and of conc HCl (18.3 ml) was heated, under stirring, at 70° C. for 1 hour. The reaction mixture was cooled at room temperature, poured into water (50 ml) and extracted with dichloromethane (2×50 ml). The organic phase was extracted with a 10% aqueous solution of sodium bicarbonate (4×50 ml). The aqueous phase was acidified with conc HCl to pH 1 and extracted with dichloromethane (3×50 ml). The combined organic phase was washed with water, anhydrified over sodium sulfate, filtered, and concentrated in vacuo.

Crystallization of the residue (0.8 g) gave the pure 2(R)-hydroxy-3(R)-[2(S)-(4-chlorophenyl)-3-methylbutanoyl]-butanedioic acid (0.4 g) (diastereisomer L).

M.P.=173°-175° C.

$^1$H-NMR (300 MHz, CDCl$_3$-TMS) delta (ppm): Diastereoisomer L (RRS) 0.56 (d, 3H, J=6.7 Hz); 0.94 (d, 3H, J=6.5 Hz); 2.20 (m, 1H, J$_{CH-CH}$=6.7 Hz, J$_{CH-CH3}$=6.5 Hz, J$_{CH-CH}$=10.4 Hz); 3.16 (d, 1H, J=10.4 Hz); 4.65 (d, 1H, J$_{CH-CH}$=2.1 Hz); 5.33 (d, 1H, J=2.1 Hz); 7.00-7.27 (AA'BB', 4H, aromatic protons).

$^1$H-NMR analysis carried out on the corresponding dimethyl ester, obtained by reaction with diazomethane, showed only the presence the diastereoisomer K (RRS).

EXAMPLE 52

Preparation of (+)-2(S)-(4-chlorophenyl)-3-methylbutanoic acid.

A mixture of the diastereoisomer K (0.9 g, 2.3 mmol), 1,4-dioxane (16 ml) and of conc HCl (16 ml) was heated, under stirring, at 90° C. for 18 hours. The reaction mixture was cooled at room temperature, diluted with water (30 ml), and extracted with dichloromethane (3×20 ml). The organic phase was extracted with a 10% aqueous solution of sodium bicarbonate (5×10 ml). The aqueous phase was acidified with conc HCl to pH 1 and extracted with dichloromethane (5×10 ml). The combined organic phase was washed with water, dried over sodium sulfate, and concentrated in vacuo.

Purification of the reaction crude (0.25 g) by column chromatography (silica gel; eluente hexane:diethylether=80:20) gave pure 2(S)-(4-chlorophenyl)-3-methylbutanoic acid 0.2 g).

$[\alpha]_D^{20}$=+38.6° (c=1%, chloroform).

EXAMPLE 53

Preparation of 2-(1(S)-bromo-2-methylpropyl)-2-(4-chlorophenyl)-1,3-dioxolane-4(R),5(R)-dicarboxylic acid A solution of the diastereoisomer 21 (10 g, 23 mmol) in dichlomethane (10 ml) was added dropwise in 15 minutes at 20° C. to a solution of sodium hydroxyde (2 g, 50.6 mmol) in water (25 ml) and methanol (100 ml). The reaction mixture was kept at 20° C. for 1 hour and the solvent removed under reduced pressure. Water (100 ml) was added. The solution, so obtained, was acidified with conc HCl to pH 1 and extracted with diethylether (3×75 ml). The organic phase was extracted with a 10% aqueous solution of sodium bicarbonate (3×75 ml). The aqueous phase was acidified with conc HCl to pH 1 and extracted with diethylether (3×75 ml). The combined organic extracts were washed with water and anhydrified over sodium sulfate. Evaporation of the solvent under reduced pressure gave the 2-(1(S)-bromo-2-methylpropyl)-2-(4-chlorophenyl)-1,3-dioxolane-4(R),5(R)-dicarboxylic acid (diastereoisomer 23) (7.2 g, 19.8 mmol; yield 86%).

$^1$H-NMR (300 MHz, CDCl$_3$-TMS) delta (ppm): diastereoisomer 23(RRS) 0.92 (d, 3H, J=6.6 Hz); 0.98 (d, 3H, J=6.2 Hz); 1.58 (m, 1H, J$_{CH-CH}$=1.8 Hz, J$_{CH-CH_3}$=6.6 Hz, J$_{CH-CH_3}$=6.2 Hz); 4.37 (d, 1H, J=1.8 Hz); 4.86 (ABq, 2H, J=6.2 Hz); 7.36–7.46 (AA'BB', 4H, aromatic protons).

The presence of one diastereoisomer was confirmed by HPLC analysis carried out on a sample of the corresponding dimethyl ester (diastereoisomer 21) obtained by reaction with diazomethane.

EXAMPLE 54

Preparation of 2-ethyl-2-(6-methoxy-2-naphthyl)-1,3-dioxolane-4(R),5(R)-dicarboxylic acid N,N,N',N'-tetraethyl amide.

A mixture of 2-ethyl-2-(6-methoxy-2-naphthyl)-1,3-dioxolane-4(R),5(R)-dicarboxylic acid dimethyl ester (9.36 g, 25 mmol), diethylamine (25 ml) and of water (20 ml) was kept, under stirring, at room temperature for 15 hours. The solvents were removed by evaporation at room temperature under reduced pressure.

Diethylether (50 ml) was added to the residue and the mixture was refluxed for 1 hour; then it was cooled at room temperature, filtered and the filtrate was dried under reduced pressure.

2-ethyl-2-(6-methoxy-2-naphthyl)-1,3-dioxolane-4(R),5(R)-dicarboxylic acid N,N,N',N'-tetraethyl amide (11 g, 24 mmol; yield 96%) was so obtained.

M.p.=108°–112° C.

$^1$H-NMR (200 MHz, CDCl$_3$-TMS) delta (ppm): 0.83 (t, 3H, J=7 Hz); 1.11 (t, 12H, J=7 Hz); 2.00 (q, 2H, J=7 Hz); 2.79 (q, 8H, J=7 Hz); 3.83 (s, 3H); 4.32 (2H, ABq, Δν=17.8, J=8 Hz); 6.9–7.8 (6H, aromatic protons).

IR (Nujol): 1605, 1630 (stretching C=O).

EXAMPLE 55

Preparation of 2-(1-bromoethyl)-2-(5-bromo-6-methoxy-2-naphthyl)-1,3-dioxolane-4(R),5(R)-dicarboxylic acid N,N,N40,N'-tetraethyl amide.

A mixture of the two diastereoisomers of 2-(1-bromoethyl)-2-(5-bromo-6-methoxy-2-naphthyl)-1,3-dioxolane-4(R),5(R)-dicarboxylic acid dimethyl ester 3 and 4 in ratio 3:4=9:1 (6.65 g, 12.5 mmol), diethylamine (27.5 ml) and of water (20 ml) was kept, under stirring, at room temperature for 15 hours. The solvents were removed under reduced pressure. Diethylether (50 ml) was added to the residue. The insoluble was filtered, washed with diethylether, and dried under reduced pressure. The diastereoisomeric mixture of 2-(1-bromoethyl)-2-(5-bromo-6-methoxy-2-naphthyl)-1,3-dioxolane-4(R),5(R)-dicarboxylic acid N,N,N',N'-tetraethyl amide 24 and 25 (6.75 g, 11 mmol; yield 88%), in ratio 24:25=9:1 (determined by $^1$H-NMR, 200 MHz).

$^1$H-NMR (200 MHz, CDCl$_3$-TMS) delta (ppm): diastereoisomer 24 (RRS): 1.06(t, 12H, J=7 Hz); 1.69(d, 3H, J=7 Hz); 2.76(q, 8H, J=8 Hz); 4.00(s, 3H); 4.55(2H, ABq, Δν=35.1, J=8 Hz); 4.54(q, 2H, J=7 Hz); 7.2–8.2(5H, aromatic protons).

EXAMPLE 56

Preparation of 2-(1-bromoethyl)-2-(5-bromo-6-methoxy-2-naphthyl)-1,3-dioxolane-4(R),5(R)-dicarboxylic acid disodium salt.

A mixture of the two diastereoisomers of 2-(1-bromoethyl)-2-(5-bromo-6-methoxy-2-naphthyl)-1,3-dioxolane-4(R),5(R)-dicarboxylic acid dimethyl ester 3 and 4 in ratio 3:4=9:1 (6.65 g, 12.5 mmol), sodium hydroxide (1 g, 25 mmol), dimethoxyethane (10 ml), and of water (10 ml) was kept, under stirring, at room temperature for 2 hours. The reaction mixture was diluted with water and extracted with diethylether. The aqueous phase was concentrated under reduced pressure to give the diastereoisomeric mixture of 2-(1-bromoethyl)-2-(5-bromo-6-methoxy-2-naphthyl)-1,3-dioxolane-4(R),5(R)-dicarboxylic acid disodium salt 26 and 27 (11.5 mmol; yield 92%) in ratio 26:27=9:1 (determined by $^1$H-NMR 200 MHz).

EXAMPLE 57

Preparation of (+)-2(S)-(5-bromo-6-methoxy-2-naphthyl)-propionic acid from a diastereoisomeric mixture of 2-(1-bromoethyl)-2-(5-bromo-6-methoxy-2-naphthyl)-1,3-dioxolane-4(R),5(R)-dicarboxylic acid 7 and 8 in ratio 7:8=93:7.

A mixture of the two diastereoisomers of 2-(1-bromoethyl)-2-(5-bromo-6-methoxy-2-naphthyl)-1,3-dioxolane-4(R),5(R)-dicarboxylic acid 7 and 8 in ratio 7:8=93:7 (9.3 g, 18.45 mmol) and of an aqueous solution (110 ml) prepared by dissolving K$_2$HPO$_4$ (26.1 g) and KH$_2$PO$_4$ (5.7 g) in water (384 ml) was heated, under stirring, at 100° C. for 21 hours. The reaction mixture was cooled at room temperature (pH 4.2), acidified with conc HCl to pH 1, and extracted with diethylether (3×100 ml). The combined organic extracts were washed with water and dried over sodium sulfate. Evaporation of the solvent under reduced pressure gave a residue that on the basis of the GLC analysis carried out on a sample treated with diazomethane was constituted of 2-(5-bromo-6-methoxy-2-naphthyl)-propionic acid (4.33 g, 14.02 mmol; yield 76%) and of the starting diastereoisomer 7 (1.3 g).

Purification by column chromatography of the reaction crude (silica gel; eluent hexane:diethylether=7:3) gave the pure (+)-2(S)-(5-bromo-6-methoxy-2-naphthyl)-propionic acid (4.22 g, 13.66 mmol; yield 74%) in 97% enantiomeric excess.

M.p.=168°–170° C.

$[\alpha]_D^{20}$=+40.8° (c=0.5%, chloroform).

HPLC analysis, carried out as described in J. Pharm. Sci. 68, 112 (1979), showed an enantiomeric ratio S(+):R(−)=98.5:1.5. The enantiomeric ratio was confirmed by $^1$H-NMR 200 MHz analysis carried out in CDCl₃ using an optically active shifting agent (europium (III) tris-[3-(eptafluoropropylhydroxymethylene)-d-camphorate]) on the corresponding methyl ester obtanined by treating a sample of acid with diazomethane.

EXAMPLE 58

A mixture of the two diastereoisomers of 2-(1-bromoethyl)-2-(5-bromo-6-methoxy-2-naphthyl)-1,3-dioxolane-4(R),5(R)-dicarboxylic acid 7 and 8 in ratio 7:8=93:7 (2.27 g, 4.5 mmol) and of an aqueous solution (31.5 ml) prepared dissolving K₂HPO₄ (26.1 g) and KH₂PO₄ (5.7 g) in water (384 ml) was heated, under stirring, at 100° C. for 42 hours. The reaction mixture was cooled at room temperature (pH 4.2) and worked up as described in example 57. (+)-2(S)-(5-bromo-6-methoxy-2-naphthyl)-propionic acid (1.32 g, 4.2 mmol; yield 93%) was obtained in 97% enantiomeric excess. The enantiomeric ratio S(+):R(−)=98.5:1.5. was confirmed by HPLC and by ¹H-NMR analysis carried out as described in example 57.

EXAMPLE 59

Preparation of the pure 2-(1(S)-bromoethyl)-2-(5-bromo-6-methoxy-2-naphthyl)-1,3-dioxolane-4(R),5(R)-dicarboxylic acid (diastereoisomer 7).

A mixture of the two diastereoisomers of 2-(1-bromoethyl)-2-(5-bromo-6-methoxy-2-naphthyl)-1,3-dioxolane-4(R),5(R)-dicarboxylic acid 7 and 8 in ratio 7(RRS):8(RRR)=94:6 (134.42 g, 0.266 mol) and of an aqueous solution (1726 ml) prepared dissolving K₂HPO₄ (174 g) and KH₂PO₄ (38 g) in water (2000 ml) was heated, under stirring, at 90° C. for 14 hours. The reaction mixture was cooled at room temperature (acidic pH), acidified with conc HCl to pH 1, and extracted with diethylether (3×150 ml). The combined organic extracts were washed with water and anhydrified over sodium sulfate. Evaporation of the solvent under reduced pressure gave a residue that was dried under vacuo at 80° C. for 12 hours. A solution of methanesulfonic acid (1 ml) in methanol (2000 ml) was added to the residue (118 g) so obtained. The solution was heated at reflux for 2 hours, cooled at room temperature, neutralized with sodium bicarbonate. The solvent was removed under reduced pressure and water (1000 ml) was added to the residue. The solution was extracted with diethylether (2×500 ml). The combined organic extracts were washed with water, dried over sodium sulfate, and concentrated in vacuo. Purification of the residue by column chromatography (silica gel; eluent hexane:diethylether=8:2) gave the pure 2-(1(S)-bromoethyl)-2-(5-bromo-6-methoxy-2-naphthyl)-1,3-dioxolane-4(R),5(R)-dicarboxylic acid dimethyl ester 3 (56 g, 0.105 mol).

A solution of sodium hydroxide (5.32 g, 0.133 mol) in water (70 ml) was added dropwise in 1 hour, under stirring, to a solution of the diastereoisomer 3 (35.4 g, 0.665 mol) in methanol (250 ml) at 20° C. The reaction mixture was kept at 20° C. for 2 hours; then methanol was removed under reduced pressure mantaining the initial volume of the solution by addition of water. The aqueous solution, so obtained, was extracted with dichloromethane, acidified with conc HCl to pH 1, and extracted with diethylether (3×100 ml). The combined organic extracts were washed with water, anhydrified over sodium sulfate, filtered, and concentrated in vacuo. Crystallization of the residue from dichloromethane gave the pure 2-(1(S)-bromoethyl)-2-(5-bromo-6-methoxy-2-naphthyl)-1,3-dioxolane-4(R),5(R)-dicarboxylic acid (diastereoisomer 7).

M.p.:=184°–186° C.

$[\alpha]_D^{20} = +39.73°$ (c=1%, acetone).

¹H-NMR (200 MHz, esadeuteroacetone-TMS) delta (ppm): 1.68(d, 3H, J=7 Hz); 4.03(s, 3H); 4.66(q, 1H, J=7 Hz); 4.95(2H, ABq, Δν=34.67 Hz, J=6.5 Hz); 7.46–8.18(m, 5H, aromatic protons).

EXAMPLE 60

Preparation of (+)-2(S)-[4-(2-methylpropyl)-phenyl]-propionic acid

A mixture of the two diastereoisomers of 2-(1-bromoethyl)-2[4-(2-methylpropyl)-phenyl]-1,3-dioxolane-4(R),5(R)-dicarboxylic acid 13 and 14 in ratio 13:14=87:13 (3.29 g, 8.2 mmol) was added to an aqueous solution (49 ml) of K₂HPO₄ (4.26 g) and KH₂PO₄ (0.93 g). The solution (pH 6.6) was heated, under stirring, at 100° C. for 68 hours. The reaction mixture was cooled at room temperature (pH 5.5), diluted with water (100 ml), acidified with con HCl to pH 1, and extracted with diethylether (3×40 ml). The organic phase was then extracted with a 10% aqueous solution of sodium bicarbonate (6×40 ml). The combined aqueous extracts were acidified with conc HCl to pH 1 and extracted with diethylether (3×50 ml). The combine organic extracts were washed with water, dried over sodium sulfate, and concentrated in vacuo. Purification by column chromatography (silica gel; eluent hexane:diethylether=8:2) gave the pure 2[4-(2-methylpropyl)-phenyl]-propionic acid (0.28 g). $[\alpha]_D^{20} = +47.9°$ (c=1%, ethanol 95%)

EXAMPLE 61

A mixture of the two diastereoisomer of 2-(1-bromoethyl)-2-[4-(2-methylpropyl)-phenyl]-1,3-dioxolane-4(R),5(R)-dicarboxylic acid 13 and 14 in ratio 13:14=87:13 (3.29 g, 8.2 mmol) was added to an aqueous solution (115 ml) of KH₂PO₄ (16.4 g) and NaOH (0.82 g). The solution (pH 5) was heated, under stirring, at 100° C. for 90 hours.

The reaction mixture was cooled at room temperature (pH 3.5) and worked up as described in example 60.

Pure 2-[4-(2-methylpropyl)-phenyl]-propionic acid (0.66 g) was obtained.

$[\alpha]_D^{20} = +48.8°$ (c=1%, ethanol 95%).

EXAMPLE 62

A mixture of the two diastereoisomers of 2-(1-bromoethyl)-2-(5-bromo-6-methoxy-2-naphthyl)-1,3-dioxolane-4(R),5(R)-dicarboxylic acid 7 and 8 in ratio 7:8=94:6 (2.52 g, 5 mmol) was added to an aqueous solution (70 ml) of KH₂PO₄ (10 g) and NaOH (1.4 g). The solution (pH 6) was heated at 90° C. for 50 hours. The reaction mixture was cooled at room temperature (pH 6.0) and worked up as described in example 57.

Pure (+)-2(S)-(5-bromo-6-methoxy-2-naphthyl)-propionic acid (1.3 g, 4.2 mmol; yield 84%) was obtained in 90% enantiomeric excess.

M.p.=168°–170° C.

$[\alpha]_D^{20} = +37.85°$ (c=0.5%, chloroform).

The enantiomeric ratio S(+):R(−)=95:5 was confirmed by HPLC and by ¹H-NMR analysis carried out as described in example 57.

EXAMPLE 63

The pure diastereoisomer 2-(1(S)-bromoethyl)-2-(5-bromo-6-methoxy-2-naphthyl)-1,3-dioxolane-4(R),5(R)- dicarboxylic acid 7 (2.52 g, 5 mmol) was added to an aqueous solution (70 ml) of KH$_2$PO$_4$ (10 g) and NaOH (1.4 g). The solution (pH 6) was heated at 90° C. for 50 hours. The reaction mixture was cooled at room temperature (pH 5.9) and worked up as described in example 57.

Pure (+)-2(S)-(5-bromo-6-methoxy-2-naphthyl)-propionic acid (1.02 g, 3.3 mmol; yield 66%) was obtained in 98% enantiomeric excess.

M.p.=168°-170° C.

$[\alpha]_D^{20}$=+40.74° (c=0.5%, chloroform).

The enantiomeric ratio S(+):R(−)=99:1 was confirmed by HPLC and by $^1$H-NMR carried out as described in example 57.

EXAMPLE 64

Comparative example at pH higher than 7.

The pure diastereoisomer 7(RRS) (2.52 g, 5 mmol) was added to an aqueous solution (70 ml) of KH$_2$PO$_4$ (10 g) and NaOH (2.5 g). The solution (pH 7.2) was heated at 90° C. for 50 hours. The reaction mixture was cooled at room temperature (pH 7.0) and worked up as described in example 57.

Pure (+)-2(S)-(5-bromo-6-methoxy-2-naphthyl)-propionic acid (0.88 g, 2,85 mmol; yield 57%) was obtained in 78% enatiomeric excess.

M.p.=166°-168° C.

$[\alpha]_D^{20}$=+32.58° (c=0.5%, chloroform).

The enantiomeric ratio S(+):R(−)=89:11 was confirmed by HPLC and by $^1$H-NMR as described in example 57.

EXAMPLE 65

Comparative example at pH higher then 7.5.

The pure diastereoisomer 7(RRS) (2.52 g, 5 mmol) was added to an aqueous solution (70 ml) of KH$_2$PO$_4$ (10 g) and NaOH (3 g).

The solution (pH 7.65) was heated at 90° C. for 50 hours. The reaction mixture was cooled at room temperature (pH 7.5) and worked up as described in example 57.

Pure (+)-2(S)-(5-bromo-6-methoxy-2-naphthyl)-propionic acid (1.03 g, 3.33 mmol; yield 67%) was obtained in 74% enatiomeric excess.

M.p.=164°-168° C.

$[\alpha]_D^{20}$=+31.20° (c=0.5%, chloroform).

The enantiomeric ratio S(+):R(−)=87:13 was confirmed by HPLC and by $^1$H-NMR as described in example 57.

EXAMPLE 66

A mixture of the two diastereoisomers 7(RRS) and 8(RRR) in ratio 7:8=94.6 (2.52 g, 5 mmol) was added to an aqueous solution (70 ml) of KH$_2$PO$_4$ (10 g) and NaOH (0.5 g).

The solution (pH 5.1) was heated at 90° C. for 52 hours. The reaction mixture was cooled at room temperature (pH 4.2) and worked up as described in example 57.

Optically pure (+)-2(S)-(5-bromo-6-methoxy-2-naphtyl)-propionic acid (1.27 g, 4.11 mmol; yield 82%) was obtained.

M.p.=167°-169° C.

$[\alpha]_D^{20}$=+42.2° (c=0.5%, chloroform).

The optical purity was confirmed by HPLC and by $^1$H-NMR as described in example 57.

EXAMPLE 67

The pure diastereoisomer 7(RRS) (2.52 g, 5 mmol) was added to an aqueous solution (70 ml) of KH$_2$PO$_4$ (10 g) and NaOH (0.5 g).

The solution (pH 5.15) was heated at 90° C. for 52 hours. The reaction mixture was cooled at room temperature (pH 4.2) and worked up as described in example 57.

Optically pure (+)-2(S)-(5-bromo-6-methoxy-2-naphthyl)-propionic acid (1.30 g, 4.20 mmol; yield 84%) was obtained.

M.p.=168°-170° C.

$[\alpha]_D^{20}$=+42.2° (c=0.5%, chloroform).

The optical purity was confirmed by HPLC and by $^1$H-NMR as described in example 57.

EXAMPLE 68

The pure diastereoisomer 7(RRS) (2.52 g, 5 mmol) was added to an aqueous solution (35 ml) prepared dissolving KH$_2$PO$_4$ (26.1 g) and KH$_2$PO$_4$ (5.7 g) in water (384 ml).

The solution was heated at 100° C. for 45 hours. The reaction mixture was cooled at room temperature (pH 4.1) and worked up as described in example 57.

Optically pure (+)-2(S)-(5-bromo-6-methoxy-2-naphthyl)-propionic acid (1.3 g, 4.2 mmol; yield 84%) was obtained.

M.p.=168°-170° C.

$[\alpha]_D^{20}$=+42.23° (c=0.5%, chloroform).

The optical purity was confirmed by HPLC and by $^1$H-NMR as described in example 57.

EXAMPLE 69

A mixture of the two diastereoisomers 7(RRS) and 8(RRR) in ratio 7:8=93:7 (2.52 g, 5 mmol) was added to an aqueous solution (70 ml) of KH$_2$PO$_4$ (10 g).

The solution (pH 4.2) was heated at 90° C. for 50 hours. The reaction mixture was cooled at room temperature (pH 3.2) and worked up as described in example 57.

Pure (+)-2(S)-(5-bromo-6-methoxy-2-naphthyl)-propionic acid (0.65 g, 2.10 mmol; yield 42%) was obtained in 94% enantiomeric excess.

M.p.=164°-165° C.

$[\alpha]_D^{20}$=+40.08° (c=0.5%, chloroform).

The enantiomeric ratio S(+):R(−)=97:3 was confirmed by HPLC and by $^1$H-NMR as described in example 57.

EXAMPLE 70

A solution of the two diastereoisomers of 2-(1-bromo-ethyl)-2-(5-bromo-6-methoxy-2-naphthyl)-1,3-dioxo-lane-4(R),5(R)-dicarboxylic acid N,N,N',N'-tetraethyl amide 24(RRS) and 25(RRR) in ratio 24:25=9:1 (2.93 g, 5 mmol) in water (70 ml) was heated at 90° C. for 50 hours. The reaction mixture was cooled at room temperature (pH 5.6) and worked up as described in example 57.

Pure (+)-2(S)-(5-bromo-6-methoxy-2-naphthyl)-propionic acid (0.58 g) was obtained in 98% enantiomeric excess.

M.p.=164°-165° C.

$[\alpha]_D^{20}$=+41.74° (c=0.5%, chloroform).

The enantiomeric ratio S(+):R(−)=99:1 was confirmed by HPLC and by $^1$H-NMR as described in example 57.

EXAMPLE 71

A mixture of the two diastereoisomers of 2-(1-bromo-ethyl)-2-(5-bromo-6-methoxy-2-naphthyl)-1,3-dioxolane-4(R),5(R)-dicarboxylic acid N,N,N',N'-tetrethyl amide 24(RRS) and 25(RRR) in ratio 24:25=9:1 (2.93 g, 5 mmol) was added to an aqueous solution (70 ml) of $KH_2PO_4$ (10 g) and NaOH (0.5 g).

The solution (pH 5.7) was heated at 90° C. for 50 hours. The reaction mixture was cooled at room temperature (pH 4.2) and worked up as described in example 57.

Pure (+)-2(S)-(5-bromo-6-methoxy-2-naphthyl)-propionic acid (0.54 g) was obtained in 98% enantiomeric excess.

M.p.=166°–168° C.

$[\alpha]_D^{20} = +41.86°$ (c=0.5%, chloroform).

The enantiomeric ratio S(+):R(−)=99:1 was confirmed by HPLC and by $^1$H-NMR as described in example 57.

We claim:

1. An enantioselective process for the preparation of an optically active alpha-arylalkanoic acid, said process comprising stereo specifically halogenating the carbon atom in the alpha-position to the ketal group in a homochiral ketal of the formula

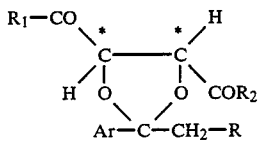

in which
  Ar represents aryl, aryl substituted by halogen, $C_1$-$C_4$ alkyl, $C_3$-$C_6$ cycloalkyl, benzyl, hydroxy, $C_1$-$C_4$ alkoxy, $C_1$-$C_4$ alkylthio, $C_1$-$C_4$ haloalkyl, $C_1$-$C_4$ haloalkoxy, phenoxy, thienylcarbonyl or benzoyl;
  R represents linear or branched $C_1$-$C_4$ alkyl;
  $R_1$ and $R_2$, which can be the same or different, represent hydroxy, $O^-M^+$, $OR_3$ or $NR_4R_5$, wherein $R_3$ is $C_1$-$C_{24}$ alkyl, $C_3$-$C_6$ cycloalkyl, phenyl or benzyl;
  $M^+$ is the cation of an alkaline metal;
  $R_4$ and $R_5$, which can be the same or different, represent hydrogen, $C_1$-$C_4$ alkyl, $C_5$-$C_6$ cycloalkyl, or $-(CH_2)_n-CH_2OH$ where n is 1, 2 or 3 or $R_4$ and $R_5$ together constitute $-(CH_2)_m-$ wherein m is 4 or 5 or $-CH_2-CH_2-R_7-CH_2-CH_2-$ wherein $R_7$ is an oxygen atom, NH or N-($C_1$-$C_4$) alkyl; and the C atoms indicated by an asterisk both have (R) or (S) configuration, said ketal being halogenated in the alpha-position to the ketal group with an achiral halogenating reagent giving an epimeric mixture of alpha-halogenketals enriched in the RRS epimer when starting from the RR un-halogenated ketal, and enriched in the SSR epimer when starting from the SS un-halogenated ketal, said alpha-halogenketal having the formula

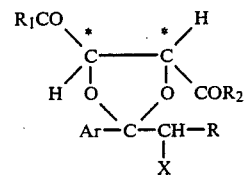

wherein:
  $A_r$, R, $R_1$ and $R_2$ are as above-defined and X is Cl, Br or I, and
  rearranging said mixture to an enantiomeric mixture of alpha-arylalkanoic acids of the formula

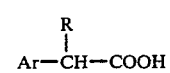

where Ar and R are as above-defined, having an enantiomeric ratio at least equal to or higher than the epimeric ratio of the starting alpha-haloketals, in a water-containing medium under acidic conditions.

2. The enantioselective process according to claim 1, wherein the halogenation step is performed with an achiral halogenating system selected from the group consisting of bromine, a quaternary ammonium perhalide, sulphuryl chloride, cupric chloride, cupric bromide, N-chloro-succinimide, pyridine perbromide, pyrrolidone perbromide, hexachloro-2,4-cyclo-hexadienone, iodine and iodine chloride, in the presence of an inert organic solvent, at a temperature between −40° and 30° C.

3. The enantioselective process according to claim 2, wherein the halogenating reagent is bromine.

4. The enantioselective process according to claim 1, wherein rearrangement of the epimeric mixture of alpha-halogen-ketals is performed in a single step at a pH between 4 and 6 and at temperature between 20° and 100° C.

5. The enantioselective process according to claim 1, wherein a ketal of the formula

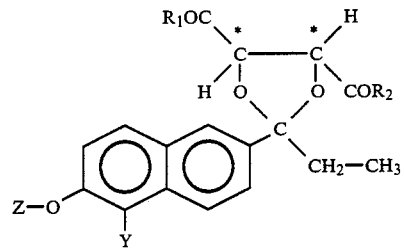

wherein $R_1$ and $R_2$ are as defined in claim 1, Y represents a hydrogen, chlorine or bromine atom and Z represents hydrogen, methyl or alkaline metal, and the C atoms indicated by an asterisk both have (R) configuration is halogenated in the alpha-position to the ketal group with an achiral halogenating agent thus giving an epimeric mixture of alpha-halogen-ketals essentially or predominantly consisting of the RRS epimer of the formula

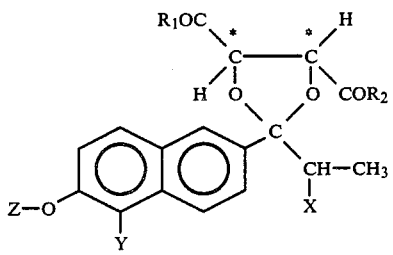 (B)

wherein $R_1$, $R_2$, Y and Z are as above defined, X represents chlorine, bromine or iodine, the carbon atoms marked by an asterisk have retained the R configuration, while the carbon atom to which X is bonded has the S configuration, and rearranging said mixture to the corresponding alpha-arylalkanoic acids of the formula

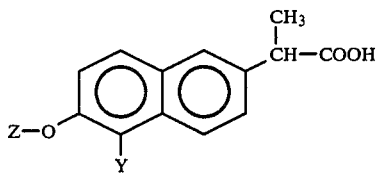

where Z and Y are as above defined, having an enantiomeric ratio substantially equal to or higher than the epimeric ratio of the starting alpha-halogen-ketals, in a water containing medium under acidic conditions.

6. The process according to claim 5, wherein the halogenation step is performed with bromine, in the presence of an inert organic solvent, at a temperature between $-40°$ and $30°$ C.

7. The process according to claim 5, wherein the rearrangement step is performed in a single step, at a temperature between $20°$ and $100°$ C.

8. The process according to claim 5, further comprising hydrogenolyzing the alpha-arylalkanoic acids when Y is chlorine or bromine.

* * * * *